US005965440A

United States Patent [19]

Reeves

[11] Patent Number: 5,965,440
[45] Date of Patent: Oct. 12, 1999

[54] CONTROLLED GENE PRODUCT DELIVERY FROM A REGULATABLE RETROVIRAL VECTOR

[75] Inventor: Steven A. Reeves, Arlington, Mass.

[73] Assignee: The General Hospital Corporation, Boston, Mass.

[21] Appl. No.: 08/568,495

[22] Filed: Dec. 7, 1995

[51] Int. Cl.[6] ............................ C12N 15/63; C12N 15/00; A01N 43/04; A61K 31/70

[52] U.S. Cl. ...................... 435/456; 435/320.1; 435/69.1; 435/69.8; 514/44

[58] Field of Search ........................... 424/93.21; 514/44; 435/69.1, 172.3, 320.1, 69.8, 91.2, 91.4, 456; 935/70, 62, 55, 57

[56] References Cited

U.S. PATENT DOCUMENTS

| | | | |
|---|---|---|---|
| 5,464,758 | 11/1995 | Gossen et al. | 435/69.1 |
| 5,654,168 | 8/1997 | Bujard et al. | 435/69.1 |

FOREIGN PATENT DOCUMENTS

| | | |
|---|---|---|
| 89/03882 | 5/1989 | WIPO . |
| WO 89/03882 A1 | 5/1989 | WIPO . |

OTHER PUBLICATIONS

O'Malley, Jr. et al., "Somatic Gene Therapy", Archives of Otolaryngology—Head & Neck Surgery, Oct. 1993, vol. 119, pp. 1100–1107, especially pp. 1104–1105.

Fishman et al., "Tetracycline–Regulated Cardiac Gene Expression in Vivo", Journal of Clinical Investigation, Apr. 1994, vol. 93, pp. 1864–1868, especially pp. 1867–1868.

Cerretti et al., "Molecular Cloning of the Interluekin–1β Converting–Enzyme", Science, Apr. 1992, vol., 256, pp. 97–100, see entire document.

Bonifacio, Maria J., et al.; Retrovirus–Mediated Gene Transfer of Transthyretin and Transthyretin–Methionine 30: A Potential Tool for the Study of Amyloidogenesis; Neuromusc. Disord., vol. 3, No. 4, pp. 275–282, 1993.

Crameri, Andreas, et al.; Efficacy of Tetracycline–Controlled Gene Expression Is Influenced by Cell Type; Benchmarks, vol. 18, No. 2, pp. 197–200 (1995).

Feigenbaum, Lionel, et al.; Regulation of the Host Range of Human Papovavirus JCV; Proc. Natl. Acad. Sci. USA vol. 84, pp. 3695–3698, Jun., 1987.

Freed, Curt R., et al., Survival of Implanted Fetal Dopamine Cells and Neurologic Improvement 12 to 46 months after Transplantation for Parkinson's Disease, New England J. of Med., vol. 327, pp. 1549–1555, Nov. 26, 1992.

Freeman, Scott M., et al.; The "Bystander Effect": Tumor Regression When a Fraction of the Tumor Mass is Genetically Modified, Cancer Research 53, 5274–5283, Nov. 1, 1993.

Furth, Priscilla, A., et al.; Temporal Control of Gene Expression in Transgenic Mice by a Tetracycline–Responsive Promoter; Proc. Natl. Acad. Sci. USA, vol. 91, pp. 9302–9306, Sep., 1994.

Gage, F.H., et al.; Grafting Genetically Modified Cells to the Brain: Possibilities for the Future; Neuroscience, vol. 23, No. 3 pp. 795–807, 1987.

Gage, Fred H., et al.; Intracerebral Grafting; A Tool for the Neurobiologist; Neuron, vol. 6, pp. 1–12, Jan., 1991.

Gossen, Manfred et al.; Tight Control of Gene Expression in Mammalian Cells by Tetracycline–Responsive Promoters; Proc. Natl. Acad. Sci. USA, vol. 89, pp.5547–5551, Jun., 1992.

Gossen, Manfred, et al.; Control of Gene Activity in High Eukaryotic Cells by Prokaryotic Regulatory Elements; Tibs 18, Dec., 1993.

Hantzopoulos, Petros A., et al.; Improved Gene Expression Upon Transfer of the Adenosine Deaminase Minigene Outside the Transcriptional Unit of a Retroviral Vector; Proc. Natl. Acad. Sci. USA, vol. 86, pp. 3519–3523, May, 1989.

Henson, John, et al.; The Transcription Factor Sp1 Bindes to the JC Virus Promoter and Is Selectively Expressed in Glial Cells in Human Brain; Anals of Neurology; vol. 32, No. 1, pp. 72–77, Jul., 1992.

Hoffmann, Barbara, et al.; Molecular Controls of Apoptosis: Differentiation/Growth Arrest Primary Response Genes, Proto–Oncogenes, and Tumor Suppressor Genes as Positive & Negative Modulators; Oncogene, vol. 9, pp. 1807–1812 (1994).

Kobayashi, Naoki, et al.; An Improved Rat Brain–Tumor Model; J. Neurosurg, 53:808–815, Dec., 1980.

Kupsch, Andreas, et al.; Neural Transplantation, Trophic Factors and Parkinson's Disease; Life Sciences, vol. 55, Nos. 25/26, pp. 2083–2095, 1994.

Lindsay, Ronald M.; Neuron Saving Schemes, Nature, vol. 373, p. 289, Jan. 26, 1995.

Louis, David N.; The p53 Gene and Protein in Human Brain Tumors; Journal of Neuropathology and Experimental Neurology, vol. 53, No. 1, pp. 11–21, Jan., 1994.

(List continued on next page.)

Primary Examiner—Deborah Crouch
Assistant Examiner—Jill D. Martin
Attorney, Agent, or Firm—Fish & Richardson P.C.

[57] ABSTRACT

An inducible or regulatable retroviral vector for the controlled delivery of a gene product, and in particular, a tetracycline regulated retroviral vector for the controlled delivery of a gene product is disclosed. This retroviral vector contains the following DNA sequences operatively linked from 5' to 3': (a) DNA comprising a first promoter; (b) DNA comprising a second promoter different from the first promoter in (a) and different from the third promoter in (e); (c) DNA encoding a tetracycline regulator unit (tTA) under the transcriptional control of the second promoter; (d) DNA comprising a tetracycline response unit (tetO) in an antisense orientation relative to the DNA encoding the regulator unit of (c); and (e) DNA comprising a third promoter different from the first promoter in (a) and different from the second promoter in (b) wherein the DNA comprising the response unit (d) is comprised within the third promoter.

35 Claims, 11 Drawing Sheets

OTHER PUBLICATIONS

Lowe, Scott W., et al.; p53 is Required for Radiation–Induced Apoptosis in Mouse Thymocytes; Nature, vol. 362, pp. 847–849, Apr. 29, 1993.

Lowe, Scott W., et al.; p53–Dependent Apoptosis Modulates the Cytotoxicity of Anticancer Agents; cell, vol. 74, pp. 957–967, Sep. 24, 1993.

Miura, Masayuki, et al.; Induction of Apoptosis in Fibroblasts by IL–1β–Converting Enzyme, a Mammalian Homolog of the C. elegans Cell Death Gene ced–3; Cell, vol. 75, pp. 653–660, Nov. 9, 1993.

Morgenstern, Jay P., et al.; A Series of Mammalian Expression Vectors and Characterisation of their Expression of a Reporter Gene in Stably and Transiently Transfected Cells, Nucleic Acids Research, vol. 18, No. 4, (Jan. 1990).

Morgenstern, Jay P., et al.; Advanced Mammlian Gene Transfer: High Titre Retroviral Vectors with Multiple Drug Selection Markers and a Complementary Helper–Free Packaging Cell Line; Nucleic Acids Research, vol. 18, No. 12, pp. 3587–3596 (May 1990).

Pear, Warren, S., et al.; Production of High–Titer Helper–Free Retroviruses by Transient Transfection; Proc. Natl. Acad. Sci. USA, vol. 90, pp. 8392–8396 (Sep. 1993).

Price, Jack, et al.; Lineage Analysis in the Vertebrate Nervous System by Retrovirus–Mediated Gene Transfer; Proc. Natl. Acad. Sci. USA, vol. 84, pp. 156–160 (Jan. 1987).

Short, M.P., et al.; Gene Delivery to Glioma Cells in Rat Brain by Grafting of a Retrovirus Packaging Cell Line; Journal of Neuroscience Research, 27:427–433 (1990).

Tada, Hiroomi, et al.,; Cell Type–Specific Expression of JC Virus Early Promotor is Determined by Positive and Negative Regulation; Journal of Virology, vol. 63, No. 1, pp. 463–466, Jan., 1989.

Thompson, Craig B., Apoptosis in the Pathogenesis and Treatment of Disease; Science, vol. 267, pp. 1456–1462, (Mar. 1995).

Thornberry, Nancy A., et al.; A Novel Heterodimeric Cysteine Protease is Required for Interleukin–1β Processing in Monocytes; Nature, vol. 356, pp. 768–774 (Apr. 1992).

Vile, Richard, et al.; Gene Transfer Technologies for the Gene Therapy of Cancer; Gene Therapy, vol. 1, pp. 88–98 (1994).

Wang, Yaolin, et al.; A Regulatory System for Use in Gene Transfer; Proc. Natl. Acad. Sci., USA, vol. 91, pp. 8180–8184 (Aug. 1994).

Wickens, Marvin, et al.; Role of the Conserved AAUAAA Sequence: Four AAUAAA Point Mutants Prevent Messsenger RNA 3' End Formation; Science, vol. 226, pp. 1045–1051 (Nov. 1984).

Yuan, Junying, et al.; The C. elegans Cell Death Gene ced–3 Encodes a Protein Similar to Mammalian Interleukin–1β–Converting Enzyme; Cell, vol. 75, pp. 641–652 (Nov. 1993).

Zigmond, Richard E., et al.; Acute Regulation of Tyrosine Hydroxylase by Nerve Activity and by Neurotransmitters via Phosphorylation; Ann. Rev. Neurosci., 12:415–61 (1989).

Orkin et al., Report and Recommendations of the Panel to Assess the NIH Investment in Research on Gene Therapy, Dec. 7, 1995.

Hanania et al., The American Journal of Medicine, vol. 99, pp. 537–552, Nov. 1995.

Marshall, Science, vol. 269, pp. 1050–1055, Aug. 25, 1995.

Anderson, Human Gene Therapy, vol. 5, pp. 281–282, 1994.

Challita & Kohn, Proc. Natl. Acad. Sci., USA, vol. 91, pp. 2567–2571, Mar. 1994.

Jaroff, Time, vol. 148, pp. 24–29, 1996.

Coghlan, Focus, vol. 148, pp. 14–15, Nov. 25, 1995.

Brown, "News Media, Researchers 'Oversold' Gene Therapy, Advisory Panel Says", The Washington Post, Dec. 8, 1995.

O'Malley et al., Archives of Otolaryngoloy—Head & Neck Surgery, vol. 119, pp. 1100–1107, Oct. 1993.

Eck & Wilson, Gene–Based Therapy. In: Goodman & Gilman's The Pharmacological Basis of Therapeutics, Ninth Edition, McGraw–Hill Health Professions Division, Chapter 5, pp. 77–101, 1995.

TETRACYCLINE REGULATABLE RETROVIRAL VECTOR

REVERSE TETRACYCLINE REGULATABLE RETROVIRAL VECTOR

CONTROLLED GENE PRODUCT DELIVERY FROM A REGULATABLE RETROVIRAL VECTOR

STATEMENT AS TO FEDERALLY SPONSORED RESEARCH

This invention was made at least in part with funds from the Federal Government, under grant number NINDS grant NS2479, and the Government therefore has certain rights in the invention.

BACKGROUND OF THE INVENTION

This invention relates to an inducible or regulatable retroviral vector for the controlled delivery of a gene product and in particular to a tetracycline regulated retroviral vector for the controlled delivery of a gene product.

The introduction of heterologous genes into cultured mammalian cells or tissues is fundamental for understanding the biochemistry, genetics and function(s) of genes and gene products. Much of the understanding of biological processes has been determined by transfection, electroporation, or viral delivery of genes into cultured cells or tissues. More recently, gene therapy approaches have emphasized the need for gene delivery vectors that can efficiently introduce, and control the expression of heterologous genes in mammalian cells.

An important feature of any gene delivery system is the ability to regulate the expression of the delivered gene. This is important in situations where the translation product of the delivered gene is being examined for its functional role in cell biology and in therapeutic situations where the gene product is toxic or must be maintained at appropriate levels. Ideally, regulation of expression of the delivered gene should be in an ON or OFF manner. Where when turned ON, gene expression should be induced and when turned OFF gene expression should be silenced.

The tetracycline-controlled transactivator responsive promoter (Tet system) is a prokaryotic inducible promoter system which has been adapted for use in mammalian cells (Gossen, M. & Bujard, H. (1992) *Proc. Natl. Acad. Sci USA*, 89, 5547–5551; Gossen, M., Bonin, A. L. & Bujard, H. (1993) TIBS 18, 471–475). In the previously developed Tet system, there are two components, each of which is carried on a separate plasmid. One component, the "response unit", is composed of the *E. coli*-derived tetracycline resistance operon regulatory elements (tetO) embedded within a minimal CMV promoter. The second component, the "regulator unit", encodes a transactivator hybrid protein (tTA) composed of the tetracycline repressor (tetR) fused to the herpes simplex virus (HSV) transactivator protein, VP16. Expression of a gene inserted downstream of the tetO/minimal CMV promoter in the response unit is highly dependent on tTA which binds tetO sequences through its tetR domain and recruits positively acting cellular transcription factors through its VP16 domain.

Gene expression is inhibited by the addition of tetracycline, which binds the transactivator protein, causing it to dissociate from the tetO/minimal CMV promoter and leading to cessation of gene transcription.

Although the Tet system has proven to be an important tool for examining the effects of genes on cells, it is limited in its applications for the following reasons:

1) For the Tet system to regulate the expression of a heterologous gene, two separate plasmids must be introduced into the cells of interest. The introduction of the two plasmids into cells is performed using chemical or electrochemical procedures that are inherently inefficient in terms of the number of cells that take up the plasmid DNAs. The limitations of these DNA transfection procedures restrict the use of the two plasmid-based Tet system to cultured cells and can not be effectively used in vivo except in the case of transgenic animals (Furth, P. A., Onge, L. S., Böger, H., Gruss, P., Gossen, M., Kistner, A., Bujard, H & Hennighausen, L. (1994) *Proc. Natl. Acad. Sci. USA*. 91, 9302–9306; Fishman, G. I., Kaplan, M. L. & Buttrick, P. M. (1994) *J. Clin. Invest.* 93 1864–1868);

2) The original two plasmid-based Tet system (Gossen, M. & Bujard, H. (1992) *Proc. Natl. Acad. Sci. USA*, 89, 5547–5551) still shows gene expression when the system is switched OFF (W. P., unpublished data; Ackland-Berglund, C. E. & Leib, D. A. (1995) *BioTechniques* 18, 196–200). This means that the Tet system allows low level uninduced gene expression, which can be a significant problem in some applications

SUMMARY OF THE INVENTION

In general, the invention features an inducible or regulatable retroviral vector for the controlled delivery of a gene product. In a preferred embodiments, this vector is a tetracycline regulated retroviral vector.

In an related aspect, this invention features a tetracycline regulated retroviral vector capable of delivering and controlling the expression of a heterologous gene in mammalian cells, including the following DNA sequences operatively linked from 5' to 3': (a) DNA comprising a first promoter; (b) DNA comprising a second promoter different from the first promoter in (a) and different from the third promoter in (e); (c) DNA encoding a tetracycline regulator unit (tTA) under the transcriptional control of said second promoter; (d) DNA encoding a tetracycline response unit (tetO) in an antisense orientation relative to said DNA encoding said regulator unit of (c); and (e) DNA comprising a third promoter different from the first promoter in (a) and different from the second promoter in (b) wherein said DNA encoding said response unit of (d) is under the transcriptional control of said third promoter.

In preferred embodiments, the first promoter (a) in the above vector is specific for the cell type or for tissue type that the vector infects. In various preferred embodiments, this first promoter of (a) is selected from the group consisting of 5' retroviral long terminal repeat promoter, Rous Sarcoma Virus (RSV), Human Immunodeficiency Virus (HIV), and phosphoglycerate kinase.

Other preferred embodiments of this vector includes DNA encoding a mammalian protein under the transcriptional control of said third promoter of (e). Preferably, such proteins are selected from the group consisting of ICE, TH, GDNF, and TH. In additional preferred embodiments, this mammalian protein is heterologous to the cells that the vector infects.

In various preferred embodiments, the addition of tetracycline either increases (enhances) or inhibits (suppresses) the expression of the mammalian gene.

In preferred embodiments, the second promoter (b) of this vector is selected from the group consisting of SV40 promoter, JC virus promoter, glial fibrillary, nestin, P0, estrogen receptor, and phosphoglycerate kinase. In other preferred embodiments, the third promoter (e) in this vector is CMV promoter or thymidine kinase.

In preferred embodiments, this vector further includes an endonuclease site located in an antisense orientation relative to the DNA encoding the regulator unit. Preferably, this endonuclease site is Xho1, Spe1, Sfi1, or Bstx1.

In preferred embodiments, this vector further includes DNA encoding a selectable marker which is under the transcriptional control of the first promoter. Preferably, the selectable marker is puromycin, neomycin, hygromycin or thymidine kinase.

In another related aspect, this invention features, a tetracycline regulated retroviral vector capable of delivering and controlling the expression of a heterologous gene in mammalian cells, including the following DNA sequences operatively linked from 5' to 3': (a) DNA comprising a first promoter; (b) DNA encoding a selectable marker under the transcriptional control of said first promoter in (a); (c) DNA comprising a second promoter different from the first promoter in (a) and different from the third promoter in (g); (d) DNA encoding a tetracycline regulator unit (tTA) under the transcriptional control of the second promoter; (e) an endonuclease site located in an antisense orientation relative to the DNA encoding said regulator unit of (d); (f) DNA encoding a tetracycline response unit (tetO) in an antisense orientation relative to the DNA encoding said regulator unit of (d); and (g) DNA comprising a third promoter different from first promoter in (a) and different from second promoter in (c) wherein the DNA encoding said response unit of (f) is under the transcriptional control of the third promoter.

In preferred embodiments, the first promoter of this vector is specific for the cell type or tissue type that the vector infects. Preferably, this first promoter is the 5' retroviral long terminal repeat promoter, Rous Sarcoma Virus, phosphoglycerate kinase or Human Immunodeficiency Virus promoter.

In preferred embodiments, this vector further includes DNA encoding a mammalian protein under the transcriptional control of the third promoter. Preferably, the mammalian protein is ICE, TH, GDNF, or TH. In additional preferred embodiments, this mammalian protein is heterologous to the cells that the vector infects.

In various preferred embodiments, the addition of tetracycline either increases (enhances) or inhibits (suppresses) the expression of the mammalian gene.

In preferred embodiments, the second promoter (c) of this vector is selected from the group consisting of SV40 promoter, JC virus promoter, glial fibrillary, nestin, P0, estrogen receptor, and phosphoglycerate kinase. In other preferred embodiments, the third promoter (g) in this vector is CMV promoter or thymidine kinase.

In preferred embodiments, this vector further includes an endonuclease site located in an antisense orientation relative to the DNA encoding the regulator unit. Preferably, this endonuclease site is Xho1, Spe1, Sfi1, or Bstx1. In preferred embodiments, the selectable marker is puromycin, neomycin, hygromycin or thymidine kinase.

In various preferred embodiments, this vector features the 5' retroviral long terminal repeat promoter as the first promoter, the puromycin resistance gene as the selectable marker, the SV40 promoter or JC virus promoter as the second promoter (c), the CMV promoter as the third promoter (g).

In another related aspect, this invention features a method of inducing apoptosis in a cell, including the steps of: (a) providing a tetracycline regulated retroviral vector containing DNA encoding the IL-1 Beta-converting enzyme (ICE), or functional homologues of ICE, under the control of tetracycline; and (b) introducing the vector into the cell.

Functional homologues of ICE include, without limitation, FAS, RIP, CPP32, ICE-II, ICE-III, and NEDD-2. In preferred embodiments, the presence of tetracycline either inhibits (suppresses) or enhances (increases) the expression of the ICE encoding DNA.

In yet another related aspect, this invention features a method of delivering a mammalian regulatable or inducible gene to a human including the steps of: (a) obtaining cells for implantation; (b) introducing into the cells of (a) a tetracycline regulated retroviral vector containing a mammalian gene under the control of tetracycline; and (c) implanting the cells of (b) into the patient.

In preferred embodiments, the cells in the above method are obtained from the patient and the presence of tetracycline either inhibits or enhances (increases) the expression of the gene. In various preferred embodiments, the gene is ICE, tyrosine hydroxylase, or glial derived neurotropic factor.

In yet another related aspect, this invention features a method of delivering a regulatable or inducible mammalian gene to a mammal including the steps of: (a) obtaining viral particles containing tetracycline regulated retroviral vectors containing the mammalian gene; and (b) infecting cells by administering the viral particles to an affected organ of the mammal. In preferred embodiments, the mammalian gene of this method is ICE, tyrosine hydroxylase, or glial-derived neurotropic factor.

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By "reporter gene" is meant a gene whose expression may be assayed; such genes include, without limitation, lacZ, amino biosynthetic genes, e.g., the yeast LEU2, HIS3, LYS2, TRP1, or URA3 genes, nucleic acid biosynthetic genes, the mammalian chloramphenicol transacetylase (CAT) gene, or any surface antigen gene for which specific antibodies are available. Reporter genes may encode any protein that provides a phenotypic marker, for example, a protein that is necessary for cell growth or a toxic protein leading to cell death, or a protein detectable by a color assay leading to the presence or absence of color. Alternatively, a reporter gene may encode a suppressor tRNA, the expression of which produces a phenotype that can be assayed. A reporter gene according to the invention includes elements (e.g., all promoter elements) necessary for reporter gene function.

By "promoter" is meant a minimal sequence sufficient to direct transcription. Also included in the invention are those promoter elements which are sufficient to render promoter-dependent gene expression inducible by the absence or presence of tetracycline in vitro or in vivo; such elements may be located in the 5' or 3' regions of the gene whose expression is sought to be controlled.

By "apoptosis" or "programmed cell death" is meant a form of cell death in which the cell activates an internal death program. It is generally characterized by nuclear DNA degradation, nuclear degeneration and condensation, and the phagocytosis of cell residua. Apoptosis of tumor cells in vivo is evidenced by tumor cell cytoplasmic reduction, detachment of tumor cells from the tumor architecture, nuclear condensation, and internucleosomal DNA fragmentation. Apoptosis in vitro is evidenced by cell shrinkage, membrane blebbing, the release of apoptotic bodies, chromosome condensation and nuclear blebbing. Apoptosis is to be contrasted with necrosis which is a form of cell death associated with external insult to the cell (e.g., poisoning or anoxia).

By "inducible" is meant a DNA sequence whose expression is mediated by the relative presence or absence of a molecule or compound. The molecule or compound may interact directly or indirectly with the DNA sequence expressed, or with another DNA sequence capable of mediating the expression of the DNA sequence. For example, in the retroviral Tet system, transactivator hybrid protein (tTA) may induce the expression of a gene inserted downstream of the tetO-minimal CMV promoter. In addition, depending upon the arrangement of DNA sequences within the retroviral TET system, the relative presence or absence of tetracycline may mediate induction of the tetO-minimal CMN promoter by competitively binding tTA. For this invention, the terms "drug regulated", "tetracycline regulated", "drug regulatable", "tetracycline regulatable", "drug inducible" and "tetracycline inducible" are used interchangeably.

By "tetracycline" is meant tetracycline ($C_{22}H_{24}N_2O_8$), a tetracycline derivative or a tetracycline analogue. Examples of tetracycline derivatives include, but are not limited to, tetracycline-HCl ($C_{22}H_{25}ClN_2O_8$), minocycline, doxycycline, oxytetracycline, chlortetracycline, tetracycline phosphate complex, tetracycline lauryl sulfate (Laruacycline) and anhydrotetracycline. For this invention, "tetracycline" and "tetracycline derivative", or "tetracycline analogues" are used interchangeably.

By "selectable marker" is meant a phenotypic characteristic by which cells having a particular genotype may be selected. For example, the presence of a gene whose expression provides resistance to a particular antibiotic allows for the selection of cells containing the gene by treating cells with the antibiotic such that non-resistant cells are killed. Examples of antibiotic resistance genes include those that confer resistance to, without limitation, ampicillin, tetracycline, chloramphenicol, puromycin, hygromycin, thymidine kinase, and neomycin. In addition to antibiotic resistance genes, selectable markers may include, without limitation, suppressor tRNA genes, amino acid biosynthetic genes, nucleic acid biosynthetic genes, and genes encoding proteins necessary for cell growth or preventing cell death.

By "ON state" and "OFF state" is meant cellular conditions under which the expression of a gene is highly induced and substantially silenced, respectively. Depending upon the organization and interactions of the DNA sequences which regulate or encode the expression of the gene product to be delivered, the ON state may be associated with either the relative presence or absence of an inducer compound. Similarly, the OFF state may be associated with the relative presence or absence of an inducer compound. Thus, a continuum of gene expression exists between the ON state and the OFF state depending upon the relative amount of inducer compound present.

By "transactivator" is meant an expression product (i.e., RNA or protein) of a DNA sequence which mediates the expression of another DNA sequence. For example, in the retroviral Tet system, expression of the DNA sequence encoding the tetracycline repressor (tetR) fused to the herpes simplex virus (HSV) transactivator protein, VP16, produces a transactivator hybrid protein (tTA) which mediates the expression of the tetO-minimal CMV promoter-gene of interest construct in the response unit. In addition, RNA transcripts from the DNA sequence encoding tTA may form duplexes with RNA transcripts from the DNA sequence encoding the response unit and thereby reduce translation of this transcript.

Therapeutic Advantages

As described herein, the invention provides a number of therapeutic advantages. As compared to traditional the dual plasmid Tet systems, a retroviral Tet system vector provides enhanced efficiency of gene delivery. The retroviral Tet vector also has reduced constitutive gene expression as compared to the dual plasmid Tet system. In addition, the precise induction of gene expression provided by the retroviral Tet system enhances the temporal and quantitative control of gene product delivery (i.e., the specification of dosage, frequency, and duration of treatment) and thus, the vector may be useful in a wide variety of gene therapy paradigms. Moreover, when directed toward gene therapy for tumors, the retroviral Tet system avoids the cytotoxicity and lack of specificity characteristic of other tumoricidal therapies (e.g., ionizing radiation and chemotherapy).

The tightly regulated expression afforded by the retroviral Tet system in vivo allows time for gene delivery (e.g., the grafting of packaging cells into the target and infection of proliferating cells) and subsequently for the precise induction of death of both target and packaging cells. Gene transduction efficiency is increased by allowing the packaging cells time to migrate and infect the target cells, while therapeutic safety is increased by the concomitant death of target and packaging cells. For example, when the retroviral Tet system is used to control the delivery of a late stage apoptosis protein (e.g., ICE) certain mechanisms of tumor cell resistance may be by-passed (e.g., p53 mutants). Genes known to regulate cell death or cell cycling may be delivered as a therapeutic agent into tumor cells by the retroviral Tet system vector.

Diagnostic Advantages

Similar to its therapeutic advantage, a retroviral Tet system provides for high efficiency gene delivery of target cells in vitro as compared to a traditional dual plasmid Tet system. Likewise, the retroviral Tet system is characterized by reduced constitutive gene expression (i.e., of the response unit) as compared to a dual plasmid Tet system. This feature is particularly useful for the in vitro investigation of negative growth influence genes (i.e., cell cycle inhibitors or dominant negative mutants). Investigation of the dose responses of cells to these and other translation products is made possible by the precise regulation of expression of the gene of interest achievable with this system. More specifically, a retroviral Tet system encoding the ICE-lacZ fusion protein may provide an in vitro model exhibiting synchronized progression toward cell death and thereby enhance the study of the biochemical events associated with apoptosis. In addition, as new cell death and growth suppressive genes and their mechanisms of action are elucidated, these genes may be used in the retroviral Tet system to study the homeostasis of cell proliferation and death.

Coupling inducible retroviral Tet system vectors with the high efficiency ecotropic BOSC23 packaging cells allows for the production of virus after a two day transient transfection and packaging reaction. In addition, the inclusion of the puromycin gene in the retroviral Tet system vectors provides for selection of puromycin resistant producer pools of BOSC23 cells from which increased viral titers may be obtained. Thus, target cells may be infected and the effect of the product of a gene of interest measured in a relatively short period of time. Moreover, because the high viral titer allows for infection of the vast majority of target cells, the need to generate stable cell lines is obviated and the potential negative selection of target cells with low tolerance for the tTA protein is diminished. Furthermore, retrovirus capable of infecting non-rodent species may be generated by the efficient "ping-pong" between ecotropic and amphotropic packaging cell lines.

Other features and advantages of the invention will be apparent from the following description of the preferred embodiments thereof, and from the claims.

A multiple cloning site containing four unique restriction sites (NotI, PacI, PmeI, BamHI) has been inserted down-stream of the response unit to facilitate the insertion of heterologous genes into the vectors. The puromycin resis-tance gene (Puro) is present in all constructs and is under the transcriptional control of the 5' retroviral LTR. The retroviral vectors are modular in that both the SV40 promoter and Puro gene can be removed and replaced by different promoters or selectable maker genes. Transcription units and direction of transcription are indicated by arrows. The vectors carrying the response gene within the 3' LTR (c,d; pBPSTR2 and pBPJTR2) are considered double copy vectors (Hantzopoulos, P A., Sullenger, B. A., G., U. & Gilboz, E. (1989) *Proc. Natl. Acad. Sci. USA.* 86, 3519–3523). The vectors carrying the response unit between 5' and 3' LTRs are single copy vectors (Panel a), Panel b): pBPSTR1, pBPJTR1). Abbreviations used: B: Babe family-based ret-roviral vector; P: puromycin gene; S: SV40 early promoter; J: JC virus early promoter; T: tTa; R: response unit. The right side of the figure is the predicted structure of the retrovirus after integration into host cell DNA (provirus).

Figure 2:
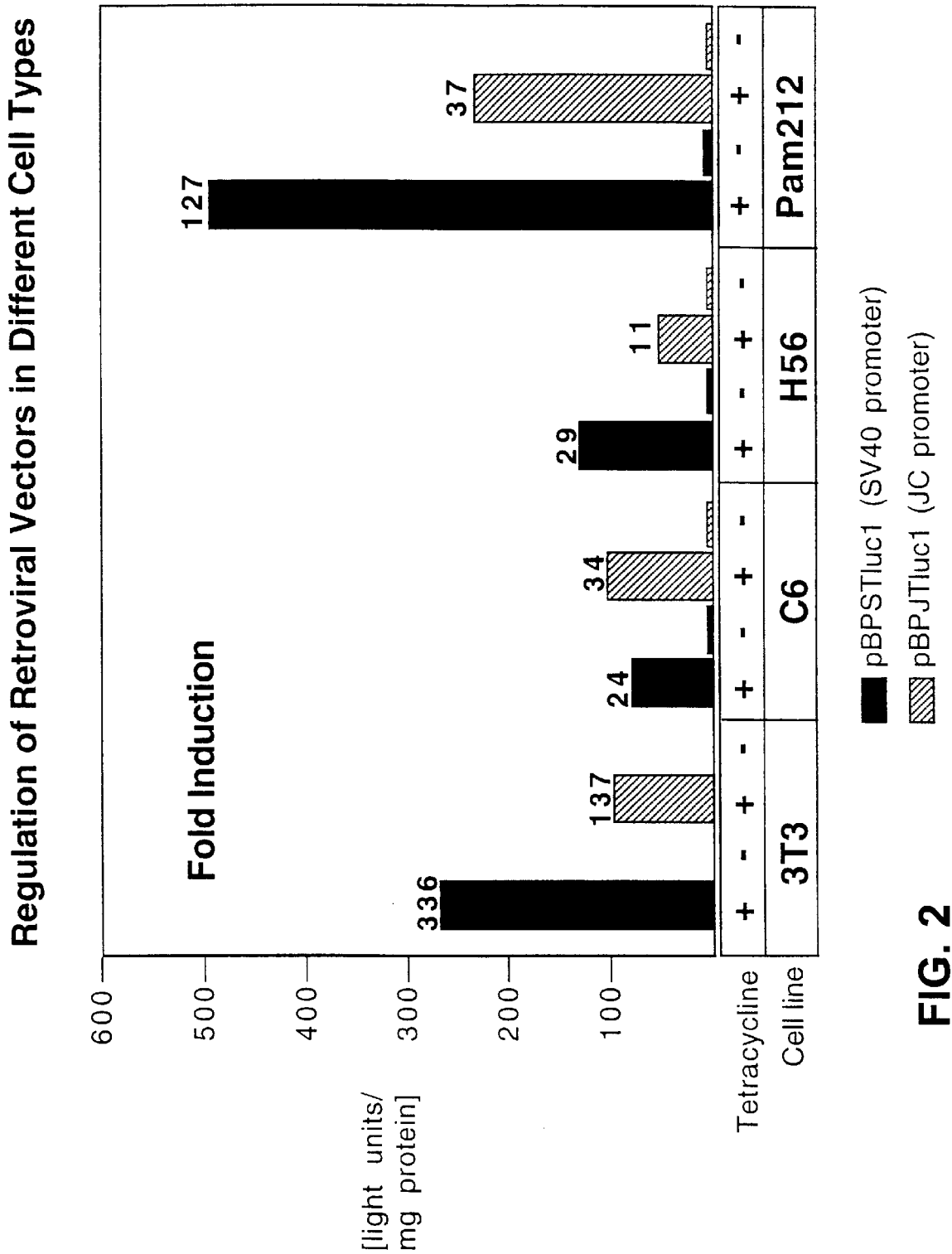

FIG. 2 is a bar graph showing the effects of the different internal promoters on gene expression and regulation. NIH 3T3, C6, H56 and Pam212 cells were infected with either pBPSTluc1 (SV40 promoter) or pBPJTluc1 (JC promoter) retrovirus. Ratios of luciferase activity in the absence (-) and presence (+) of tetracycline during and after infection reflect inducible regulation (shown above boxes). Values were obtained from Table 2 and are presented in a graphic manner.

FIG. 3 (A) is a diagram of the ICE-lacZ-containing tetracycline regulated retroviral vector used in the experi-ments. The puromycin resistance gene (Puro) is under the control of the promoter within the 5'-LTR. The murine ICE-lacZ fusion gene is cloned into the response unit and is under the transcriptional control of *E. coli*-derived tetracy-cline resistance operon regulatory elements (tetO) embed-ded within a minimal CMV promoter (minCMV). The regulator unit encodes a transactivator hybrid protein (tTA) composed of the tetracycline repressor (tetR) fused to the herpes simplex virus transactivator protein, VP16, and is under the transcriptional control of the constitutively active SV40 promoter (SV). In the absence of tetracycline, tTA protein binds tetO sequences within the response unit via its tetR domain and activates transcription of the ICE-lacZ gene. In the presence of tetracycline, which binds tTA, tTA dissociates from the response unit and transcription of the ICE-lacZ gene is inhibited. Arrows indicate the direction of transcription.

FIG. 3 (B) is a bar graph showing beta galactosidase enzyme assay. Values were 0.711±0.035 (0 time point; i.e. tetracycline not removed), 4.965±0.094 (12 hours after removal of tetracycline) and 27.046±0.626 (24 hours after removal of tetracycline) milliunits B-gal/mg protein (means±sem). Fold induction is shown above each bar.

FIGS. 4A–I are photographs and a bar graph showing the induction of apoptosis in 9L-ICE-lacZ cells. Panels A to C: After 24 hours in the presence or absence of tetracycline, expression of ICE-lacZ in 9L-ICE-lacZ cells or lacZ in 9L-lacZ cells, was determined by staining with X-gal. Panel A: 9L-ICE-lacZ cells with tetracycline. Panel B: 9L-ICE-lacZ cells without tetracycline. Panel C: 9L-lacZ cells with-out tetracycline. Panels D to F: Viability assay using calcein-AM and propidium iodide. Panel D: 9L-ICE-lacZ cells with tetracycline showing green fluorescence from the cytoplasm of viable cells. Panel E: 9L-ICE-lacZ cells in the absence of tetracycline for 24 hours, showing intense red fluorescence resulting from propidium iodide uptake into nuclei of dead cells. Panel F: Magnified view of 9L-ICE-lacZ cells without tetracycline demonstrating rhodamine fluorescence and showing highly condensed chromatin blebbing outward through the vesiculated nuclear membrane. Panels G and H: Hoescht stain of nuclei. Panel G: 9L-ICE-lacZ cells with tetracycline revealing normal nuclei. Panel H: 9L-ICE-lacZ cells in the absence of tetracycline for 24 hours revealing condensed chromatin. Panel I: 9L-ICE-lacZ cells were incu-bated with and without tetracycline for 24 hours and cell death was determined as described above. Percents of dead red cells relative to all cells counted are noted. Mean percents cell death were 96.6%±0.302 without tetracycline and 1.30%±0.446 with tetracycline (means±sem). Magnifications, A–C, ×100, D-E, ×50, F–H, ×100.

FIG. 5A–G are photographs and a graph showing the induction of apoptosis in 9L gliosarcoma tumors containing the ICE-lacZ gene. Panel A to G: 9L-ICE-lacZ cells were stereotactically implanted in the right striatum in Fisher rats on tetracycline. After administration of oral tetracycline for 7 days, tetracycline was removed for the noted time periods, and the animals were sacrificed thereafter. X-gal histochem-istry was performed on coronal brain sections and counter-stained with neutral red. Panel A: Two days after removal of tetracycline. Edge of 9L-ICE-lacZ tumor bordering normal brain parenchyma showing individual lacZ positive cells with rounded apoptotic phenotype. Panel B: Edge of 9L-ICE-lacZ tumor in comparable time point animal main-tained on tetracycline showing absence of lacZ positive cells Panel C: Four days after removal of tetracycline. Whole coronal brain section of animal showing lacZ positive cells in all regions of the tumor. Note also the areas of cell death, particularly within the central part of the tumor, but also radiating out toward peripheral areas. Panel D: Whole coronal brain section of comparable time point animal maintained on tetracycline. Note the lack of lacZ positive cells and absence of areas of cell death. Panel E: Four days after removal of tetracycline. Essentially all cells within the tumor are lacZ positive. Also note the nuclear heterogeneity, typical of apoptotic cells. Panel F: Four days after removal of tetracycline. Apoptotic lacZ positive cells in central area of the tumor and area of intense cell death. Panel G: Nine days after removal of tetracycline. In situ analysis of DNA fragmentation in individual cells in area of cell death detected by horseradish peroxidase-digoxigenin nucleotide labeling of 3'-OH DNA ends. Panel H: Subcutaneous growth of 9L-ICE-lacZ tumor on and off tetracycline. The group maintained on tetracycline is shown by black squares and the group taken off tetracycline is shown by blue circles.

There was a significant difference in subcutaneous tumor growth in animals that were taken off tetracycline compared to those left on the drug for the last two measured time points (P<0.05, one-tailed t-test). Magnifications A-B, ×100, E–G, ×100.

Figure 6A:
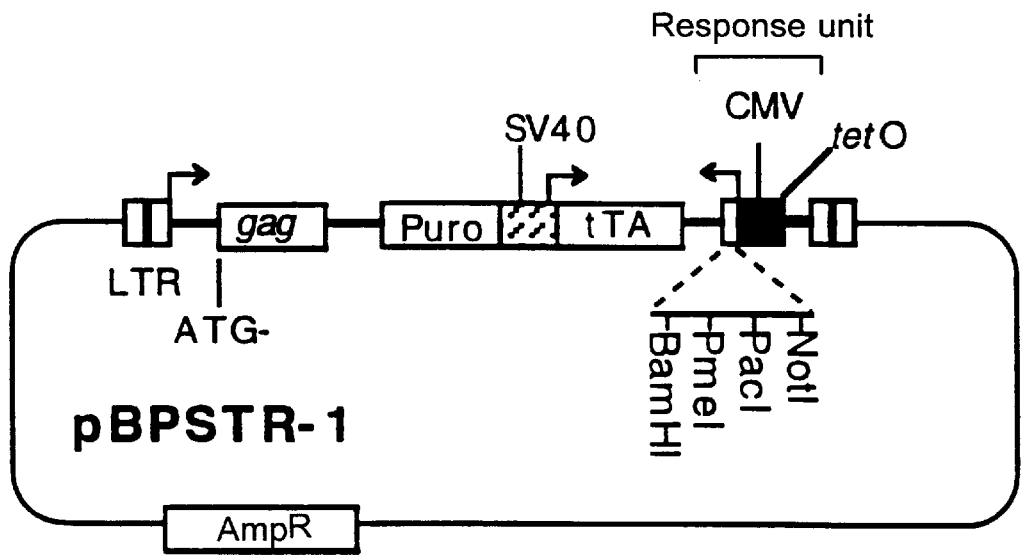

FIG. 6A is a diagram of the original tetracycline regulatable retroviral vector, pBPSTR-1, as described in Example 1. Using this vector the expression of a gene inserted into the multiple cloning site of the response unit is dependent on tTA protein binding to tetO sequences in the response unit.

Figure 6B:
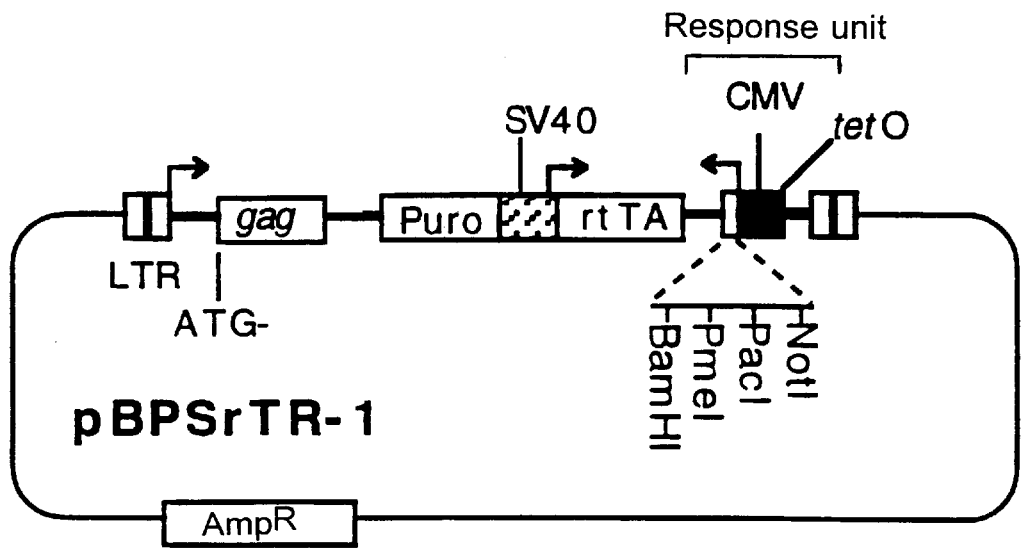

FIG. 6B is a diagram of the "reverse" tetracycline regulatable retroviral vector, pBRSrTR-1. Using this vector, expression of a gene inserted into the multiple cloning site of the response unit is dependent on "reverse" tTA (rtTA) protein binding to tetO sequences in the response unit. The reverse tTA (rtTA) protein is different than the tTA protein present in the original retroviral vector (pBPSTR-1) because it needs to bind tetracycline for it to also bind tetO sequences and activate expression of a gene in the response unit.

Figure 7:
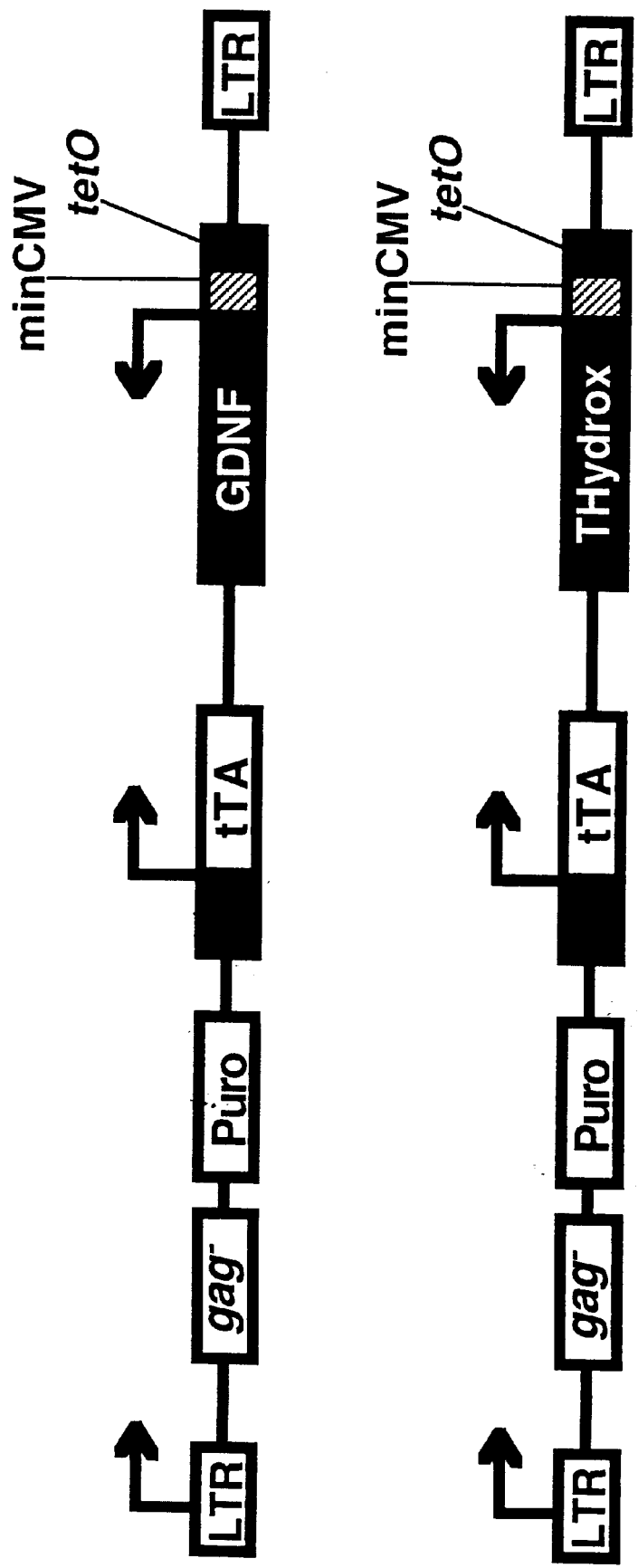

FIG. 7 are diagrams of the GDNF and TH containing tetracycline regulated retroviral vectors.

Figure 8A:
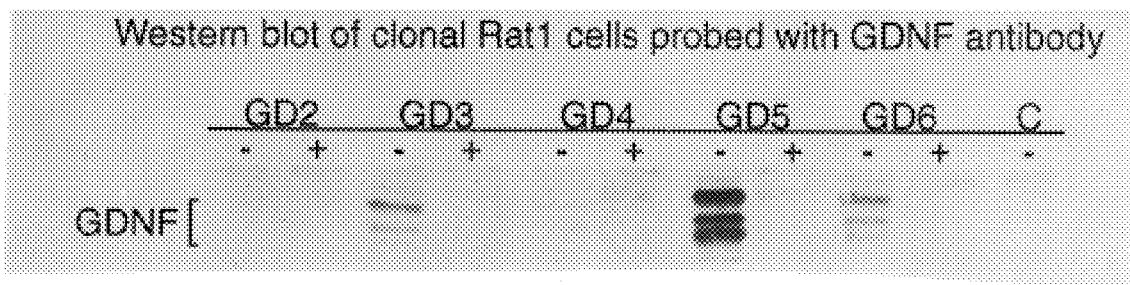
Figure 8B:
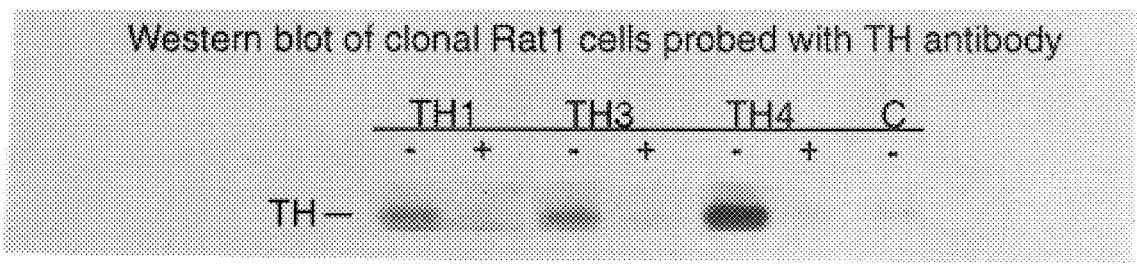

FIG. 8A-B is a photograph of the expression of GDNF and TH, in the presence or absence of tetracycline as shown by a western blot. Infected and puromycin-resistant Rat1 fibroblasts clones were examined for tetracycline dependent regulated expression of the GDNF (FIG. 8A, clones GD2, GD3, GD4, GD5, GD6) and TH genes (see FIG. 8B, clones TH1, TH3 and TH4). Shown in FIGS. 8A and 8B are western blots of protein from puromycin resistant clones that had been selected from pools of Rat1 cells that have been infected with the tetracycline regulatable retrovirus. Clones GD2, GD3, GD4, GD5, GD6, TH1, TH3, TH4 are different Rat1 clones selected with puromycin as described in the above Examples. To assay tetracycline regulation of TH and GDNF genes in the clones, cells were grown in the presence ("+") or absence ("−") of tetracycline for two days. Protein lysates were then prepared and equal amounts of total protein were examined in western blotting analysis using antibodies against either GDNF (A) or TH (B). "C" is the non-infected Rat1 control cells.

DETAILED DESCRIPTION

An inducible or regulatable retroviral vector may be used to regulate the expression of a gene of interest which is operably linked to regulatory sequences within the retroviral vector. The vector may be used in vitro or in vivo to infect cells in which the controlled delivery of a gene product is desired. The retroviral vector includes the Tet system operably linked to a gene of interest such that the transcription and translation of the gene may be regulated by altering the concentration of tetracycline in cells infected with the retroviral vector. Using this system, the amount of gene product is proportional to the amount of tetracycline administered to the cell. Thus, precise control of the delivery of gene products from a wide variety of genes may be accomplished.

In a preferred embodiment, the retroviral vector includes the Tet response unit containing the tetO sequence operably linked to a promoter capable of controlling the transcription of a gene of interest. The response unit may also include a polylinker, containing restriction sites unique to the retroviral construct, to facilitate the insertion of genes of interest into the retroviral vector. In addition, an SV40 polyadenylation signal may be operatively linked to the gene of interest to facilitate transcription thereof. Other suitable polyadenylation signals include, without limitation, AUUAAA, AAUUAA, AAUACA, AAUAAC, and CAUAAA (Wickens, et al (1984) Science, 226:1045–1050). In a preferred embodiment, the CMV promoter is the cytomegalovirus promoter (CMV), however, other suitable promoters include, without limitation, the thymidine kinase promoter. The CMV promoter preferably controls the expression of a DNA sequence encoding the ICE-lacZ fusion protein, but may also be operably linked to one of many different other genes of interest, including, without limitation, ICE, TH, GDNF, and TH.

The retroviral vector also includes the Tet regulator unit which contains the tetR coding sequence operably linked to the HSV transactivator protein, VP16, collectively under the control of an SV40 promoter. Alternatively, the tetR-HSV transactivator hybrid protein (tTA) may include transactivator proteins such as myc, Rb, p53. Moreover, the regulator unit may be alternatively under the transcriptional control of the glial fibrillary acidic protein, nestin, P0, estrogen receptor, phosphoglycerate kinase promoters In a preferred embodiment, the regulator unit and the response unit are oriented anti-sense to one another, however, they may, alternatively, be in a sense orientation. In addition, the retroviral vector includes the 5' and 3' LTRs of the Moloney Murine Leukemia virus. Other sources of 5' and 3' LTRs include, without limitation, Rous Sarcoma Virus (RSV) and Human Immunodeficiency Virus (HIV). The retroviral vector also includes a mutated form of the gag gene region to allow for packaging of the retroviral vector with a packaging cell line such as BOC23 cells. The retroviral vector may also include a selectable marker such as the puromycin gene. Alternative selectable markers include, without limitation, hygromycin, neomycin, thymidine kinase. Moreover, the retroviral vector may include a second response unit positioned within or outside the 5' or 3' LTR.

The organization and orientation of the constituent elements of the retroviral vector may be varied depending upon the type of control desired. For example, positive control of gene expression (i.e., where gene product concentration is directly proportional to inducer concentration) may be accomplished by replacing the tTA gene in the same transcriptional orientation with a functionally reverse acting tTA gene. Retroviral vectors organized in this manner are particularly useful for the intermittent delivery of positive growth factors (e.g., epidermal growth factor, platelet-derived growth factor, insulin, growth hormone) because administration of the inducer compound is only required when gene product delivery is desired. Thus, retroviral vector constructs can be designed such that the presence of an inducer, e.g., tetracyline, enhances transcription thereby increasing expression of the desired protein ("reverse tTA" or "rtTA"). The "reverse" tetracycline regulated retroviral vector of this invention can be designed to produce certain desired growth factors, hormones, growth suppressive factors, immunoproliferative, immunosuppressive and immunosupportive factors, and neurotrophic factors that can aid in the maintenance, survival and differentiation of neuronal and non-neuronal cell types.

Alternatively, negative control of gene product delivery (i.e., where the gene product concentration is inversely proportional to inducer concentration) is particularly useful for the delivery of negative growth factors (e.g., cell death or growth suppressive genes) because the expression of such genes may be suppressed or silenced by administration of the inducer compound until cell death is desired. Genes particularly suitable for use in a negatively controlled retroviral system include, without limitation, tumor or growth suppressive genes: p53, Rb, p107, p21, p16, p27 and genes functionally related to ICE; examples being FAS, RIP, CPP32, ICE-II, ICE-III, NEDD-2. Such genes may have widespread diagnostic and therapeutic uses.

In general, the drug regulated retroviral vector of this invention is used to control the expression of gene transcription. For example, tetracycline can regulate transcription and therefore the expression of a desired mammalian gene. The tetracycline regulated retroviral vector of this invention is generally designed to contain the following components, operationally linked from 5' to 3': (a) DNA comprising a first promoter; (b) DNA comprising a second promoter different from the first promoter in (a) and different from the third promoter in (e); (c) DNA comprising a tetracycline regulator unit (tTA) under the transcriptional control of the second promoter; (d) DNA encoding a tetracycline response unit (tetO) in an antisense orientation relative to the DNA encoding the regulator unit of (c); and (e) DNA comprising a third promoter different from first promoter in (a) and different from second promoter in (b) wherein said DNA encoding the response unit of (d) is under the transcriptional control of the third promoter.

Listed below are some applications for the drug regulatable retroviral vectors of this invention in humans. This list is intended to serve as examples of different applications using the vectors of this invention and is not intended to limit the invention whatsoever.

1) The drug regulated retroviral vectors of this invention can be used to deliver and express cytotoxic gene(s) to a tumor or to a diseased tissue for controlled killing of the tumor or diseased cells. These cytotoxic gene(s) include, but are not limited to, genes that encode products that are directly toxic to a specific tumor or to diseased cells, or those genes which encode products that are toxic to the tumor or to the diseased cells, in the presence of a prodrug that requires the product of the delivered gene for activation, by disrupting any aspect of the tumor or diseased cell machinery that is essential for tumor or diseased cell survival. These genes include, but are not limited to, ICE, bacterial toxins, thymidine kinase and cytosine deaminase.

2) The drug regulated retroviral vectors of this invention can be used to deliver and express therapeutic gene(s) to a tumor or diseased cells for cytostatic growth control of the tumor or diseased cells. Examples of therapeutic gene(s) are those genes that encode products that can arrest the growth or proliferation of tumor or diseased cells, but not kill the tumor or diseased cell. These therapeutic genes include, but are not limited to, p53, Rb, p21 and p16.

3) The drug regulated retroviral vectors of this invention can be used to deliver and express deliver of therapeutic gene(s) to diseased cells for replacement of deficient, defective, or lacking gene product. Therapeutic gene(s) are those genes that encode products that can replace the product of a gene that is defective or absent in diseased cells. Examples of therapeutic genes can be those genes that encode growth factors, growth suppressive factors, immunoproliferative, immunosuppressive and immunostimulative factors, and neurotrophic factors that can aid in the maintenance, survival and differentiation of neuronal and non-neuronal cell types.

4) The drug regulated retroviral vectors of this invention can be used to deliver and express programmed cell death gene(s) (e.g., genes that induce apoptosis) in tumor or diseased cells for induction of programmed cell death in tumor or diseased cells.

5) The drug regulated retroviral vectors of this invention can also be used for ex vivo or in situ infection and delivery of therapeutic gene(s) to supportive cells that can be reimplanted into individuals for the eventual controlled release of the therapeutic drug(s). Examples of therapeutic genes can be those genes that encode growth factors, growth suppressive factors, immunoproliferative, immunosuppressive and immunosupportive factors, and neurotrophic factors that can aid in the maintenance, survival and differentiation of neuronal and non-neuronal cell types. This list of examples is not intended to limit the invention.

6) The drug regulated retroviral vectors of this invention can also be used to deliver therapeutic gene(s) in utero, in situ, or ex vivo to human embryonic cells for replacement of deficient, defective, or lacking gene product(s).

Listed below are some applications for the drug regulatable retroviral vectors of this invention in the production of pharmaceuticals or drugs that could benefit humans or livestock. This list is intended to serve as examples of different applications using the vectors of this invention and is not intended to limit the invention whatsoever.

1) The drug regulated retroviral vector of this invention can be used to generate eukaryotic cells that can be grown in culture, or transgenic animals, that can produce therapeutic drug(s) in a controlled manner. Any gene that can produce a product that has adverse effects on the eukaryotic producer cells grown in culture, or transgenic animals, would be a candidate for delivery and regulated expression by the drug regulatable retroviral vector of this invention.

2) The drug regulated retroviral vector of this invention can be used to deliver genes that produce a product the can increase or decrease that body weight or body fluids of animals used in agribusiness or agriculture 3) The drug regulated retroviral vector can be used to screen for and isolate novel genes that normally when expressed in eukaryotic cells are cytostatic or cytoxic (e.g. tumor or growth suppressive genes and programmed cell death genes). The ability to inhibit the expression of a cytostatic or cytoxic gene(s) during screening and isolation will facilitate the isolation of these types of genes.

The following examples are presented to illustrate, without limitation, the invention.

EXAMPLE 1

Self-Contained, Tetracycline Regulated Retroviral Vector System for Gene Delivery to Mammalian Cells Tetracycline regulated retroviral vectors were designed and constructed to contain the tetracycline-inducible Tet system. The two components of the Tet system were organized within the vectors in a manner that stringently maintains tetracycline-dependent regulation.

I. Methods Used in the Following Experiments

A. Construction of Retroviral Plasmids

The retroviral constructs described here are derived from a modified version of pBabePuro which is a Moloney murine leukemia virus-based vector containing a puromycin resistance gene under the control of an internal SV40 promoter (Morgenstern, J. P. & Land, H. (1990) *Nucl. Acid Res.* 18, 3585–3596; Morgenstern, J. P. & Land, H. (1990) *Nucl. Acid Res.* 18. 1068). The puromycin resistance gene in pBabePuro was excised with HindIII and ClaI and replaced by the tTA gene. To do this the entire 1017-bp coding sequence of tTA was generated by PCR amplification using the pUHD15-1 plasmid (Gossen, M. & Bujard, H. (1992) *Proc. Natl. Acad. Sci USA*, 89:5547–5551) as template and primers corresponding to bp 774–790 (including a HindIII restriction site and the optimal Kozak sequence CCACCATG) and bp 1790–1774 (including a ClaI site). This pBabe-based plasmid coding for tTA under the control of the internal SV40 promoter was designated pBST. To obtain the pBJT plasmid, where the tTA gene is under the control of the JC promoter, the SV40 promoter in pBST was removed by excision with NotI and HindIII, and replaced by a 299-bp HindIII/NotI fragment from pCR1000-Mad-l corresponding to the JC virus Mad-l strain early promoter (Henson, J., Saffer, J. & Furneaux, H. (1992) *Ann. Neurol.* 32:72–77). The puromycin resistance gene, isolated as a 660-bp HindIII-/ClaI fragment from pBabePuro, was then re-inserted into the BamHI/NotI polylinker site of pBST and pBJT (located 5' to the SV40 and JC promoters) by blunt-end ligation after filling-in with Klenow, thereby destroying the NotI and BamHI sites. The resulting plasmids were designated pBPST and pBPJT, respectively.

The response plasmid pUHD 10-3 contains the heptamerized tetO sequences, a minimal CMV promoter, a cloning site for insertion of the gene of interest and an SV40 polyadenylation signal (Gossen, M. & Bujard, H. (1992) *Proc. Natl. Acad. Sci USA*, 89:5547–5551). To facilitate cloning of genes into the response cassette within the retroviral plasmids, the cloning site in pUHD 10-3 was replaced with a polylinker containing restriction sites unique to the retroviral constructs; to this end, a SacII-NotI-PacI-PmeI-BamHI adaptor (5'-GGCCGCTTAATTAAGTTTAAACG-3' (SEQ ID NO:1) and 5'-GATCCGTTTAAACTTAATTAAGCGGCCG-3') (SEQ ID NO:2) was ligated into the SacII/BamHI cloning site of pUHD 10-3. The 857-bp HinPI fragment of this modified response cassette (including tetO sequences, minimal CMV promoter, polylinker and SV40 polyadenylation signal) was then inserted into pBPST or pBPJT in an anti-sense orientation (relative to the tTA transcription unit) into either the ClaI site (located immediately downstream of the tTA gene; -I series of plasmids) or, using Klenow fill-in and blunt-end ligation, into the BglII site (located within the U3 region of the 3'-LTR, 36 bp downstream from the 5' end of the LTR; -2 series of plasmids). The SV40 polyadenylation signal, derived from the pUHD10-3 plasmid and included in the HinPI fragment that had been inserted into the retroviral plasmids, was removed by excision of a 135-bp fragment containing the relevant polyadenylation sequences with BamHI and HpaI, and replaced by a BamHI/SmaI adaptor (5'-GATCCCCCGGG-3' (SEQ ID NO:3) and 5'-CCCGGGG-3' (SEQ ID NO:4)). Depending on the promoter responsible for transcription of the tTA gene (SV40 or JC) and the location of the response unit, the resulting retroviral cloning vectors were designated pBPSTRl , pBPJTRI, pBPSTR2 and pBPJTR2.

To construct the retroviral reporter plasmids pBPSTIucl, pBPJTlucl, pBPSTluc2 and pBPJTluc2, the 1700-bp gene for firefly luciferase was excised from pGEM-luc (Promega, Madison, Wis.) with NotI and StuI and inserted into the NotI/PmeI polylinker site of the four retroviral cloning vectors.

B. Cell Culture

The following cell lines were used: rat C6 glioma cells (American Type Culture Collection (ATCC), Rockville, Md.), mouse NIH 3T3 fibroblasts (ATCC), rat H56 hepatoma cells (Bonifacia, M. J., Ezzeddine, D., Sakaki, Y., Breakefield, X. O. & Saraiva, M. J. (1993) *Neuromusc. Disord.* 3:275–282), mouse Pam212 squamous carcinoma cells (Yuspa, J., Saffer, J. & Furneaux, H. (1992) *Ann. Neurol.* 32:72–77), and the ecotropic packaging cell line BOSC23(11). C6 glioma cells were grown in Ham's F10 medium (Mediatech, Washington, D.C.) containing 15% horse serum (Sigma, St. Louis, Mo.), 2.5% fetal calf serum (Sigma), and penicillin G/streptomycin sulfate (100 units/ml and 100 $\mu$/ml, respectively) (Sigma). The other cell lines were maintained in Dulbecco's modified Eagle's minimal essential medium (Mediatech) supplemented with 10% fetal calf serum and penicillin G/streptomycin sulfate.

C. Transfections, Infections and Determination of Viral Titer

Transfections of BOSC23 cells were performed essentially as recommended (Pear, W. S., Nolan, G. P., Scott, M. L. & Baltimore, D. (1993) *Proc. Natl. Acad. Sci. USA*. 90:8392–8396). Briefly, $5\times10^6$ BOSC23 cells were plated in 10 ml medium per 100-mm dish. After 24 hours, the medium was replaced with 5 ml fresh medium. After an additional 3 hours, cells were transfected with 15 $\mu$g retroviral plasmid DNA using the calcium phosphate precipitation technique. Just prior to transfection, chloroquine was added to a final concentration of 25 $\mu$M. Six hours post-transfection, the cells were washed twice and 10 ml medium was added. Twenty-four hours post-transfection, the medium was removed and 5 ml of fresh medium was added. The medium containing the virus was removed 48 hours post-transfection, filtered through a 0.45-$\mu$m filter and either used directly or stored frozen until use. Media from different plates containing BOSC23 cells transfected with the same retroviral construct were pooled to provide a common stock of viral titer for each set of experiments. BOSC23 cells were grown in either the presence (1 $\mu$g/ml, Sigma) or absence of tetracycline during packaging of virus.

Cells which had been plated at a density of $5\times10^5$ per 100-mm dish the day before infection, were infected in the presence of polybrene (4 $\mu$g/ml, Sigma) with 5 ml of filtered medium containing virus. After 4 hours, the medium was aspirated and fresh medium was added. Cells were washed twice 20 hours post-infection and luciferase assays were performed 48 hours post-infection. To study tetracycline-dependent regulation of gene expression, cells were grown in the presence (1 $\mu$g/ml) or absence of tetracycline from 3 hours before infection until harvesting. All experiments were performed at least twice in duplicate.

For titering, NIH 3T3 cells were infected with serial dilutions of filtered BOSC23 supernatant. Cells were split 1:10 into selection medium containing puromycin (1.5 $\mu$g/ml, Sigma) 48 hours post-infection. Fresh media was added every 3 days, and colonies were counted 12 days later after fixation and Giemsa staining.

D. Luciferase Assay

Cells were washed three times in phosphate buffered saline and then lysed in 1 mM dithiothreitol/1% Triton X-100/luciferase buffer (25 mM glycylglycine, 15 mM MgSO$_4$,4 mM EGTA, pH 7.8) at 4° C. Cell lysates were collected from plates with a cell scraper and centrifuged for 4 min at 7,800×g. Aliquots (100 $\mu$l) of the supernatant were mixed with 370 $\mu$l luciferase buffer containing 2 mM ATP, l mM dithiothreitol and 15 mM potassium phosphate, pH 8.3, and assayed for luciferase activity in a 1251 luminometer (Wallac, Gaithersburg, Md.) using the integral mode. D-Luciferin (Sigma) was used at a saturating substrate concentration (0.2 mM in luciferase buffer). Luciferase activity was adjusted to protein content of the lysates, as determined according to Lowry.

II. Results

A. Construction of Retroviral Vectors

To incorporate the tetracycline inducible system into a retroviral vector, a retroviral vectors containing the tTA gene under the control of either the broadly active SV40 promoter or the glial specific JC virus promoter was first constructed (Feigenbaum, L., Khalili, K., Major, E. & Khoury, G. (1987) *Proc. Natl. Acad. Sci. USA*. 84 3695–3698; Tada, H., Lashgari, M., Rappaport, J. & Khalili, K. (1989) *J. Virol.* 63, 463–466) (regulator unit). An important consideration for efficient regulation of a gene inserted into the response unit is where to insert this unit relative to the promoters within the regulator unit and the 5'-LTR of the virus. For the Tet system to function efficiently, the response unit must operate independently of other promoters within the virus. Two different cloning strategies were used to determine the optimal placement of the response unit within the retroviral vectors. In all of these constructs the luciferase gene was inserted into the response unit to allow quantitation of tetracycline-dependent regulation.

Figure 1A:
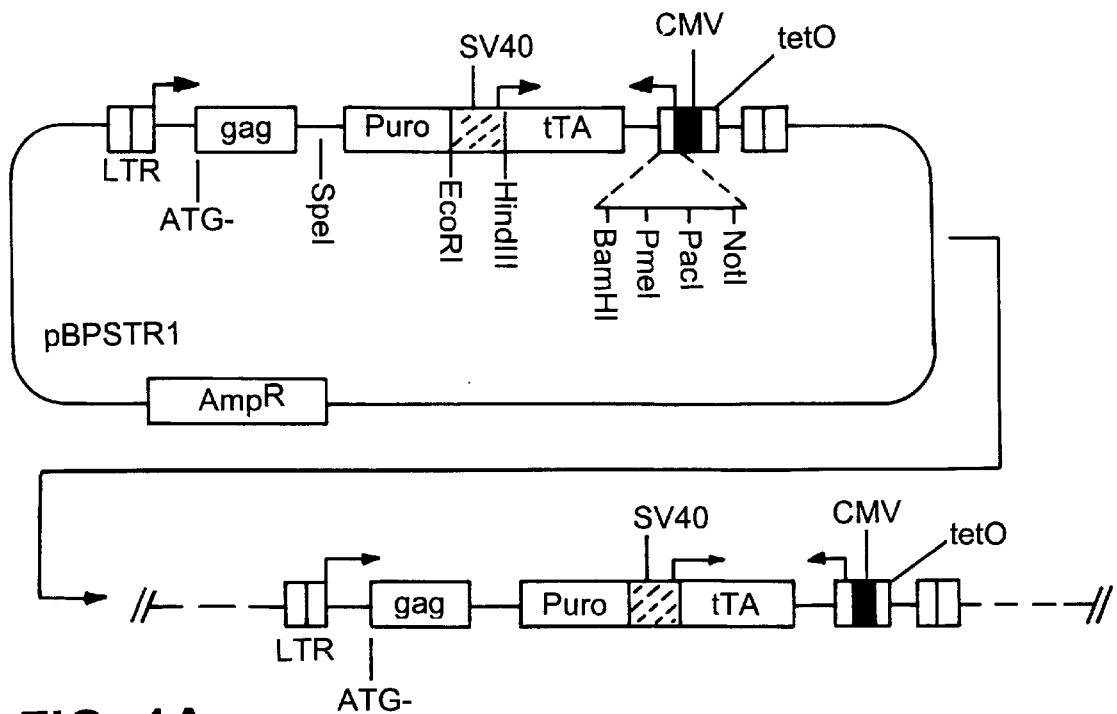
FIGS. 1A–D diagrams the inducible and cell-specific retroviral cloning vectors used in Examples 1 and 2. All retroviral vectors contain both components of the Tet system including the regulator unit [containing the tTA (tetracycline-responsive tansactivator) gene] which is under the tanscriptional control of internal SV40 or JC virus promoters, and the response unit which is under the tran-scriptional control of a minimal CMV promoter (lacking enhancers) containing seven tet operators (tetO) Note that the response unit is inserted into the retroviral vectors in an antisense orientation relative to the regulator unit.
Figure 1B:
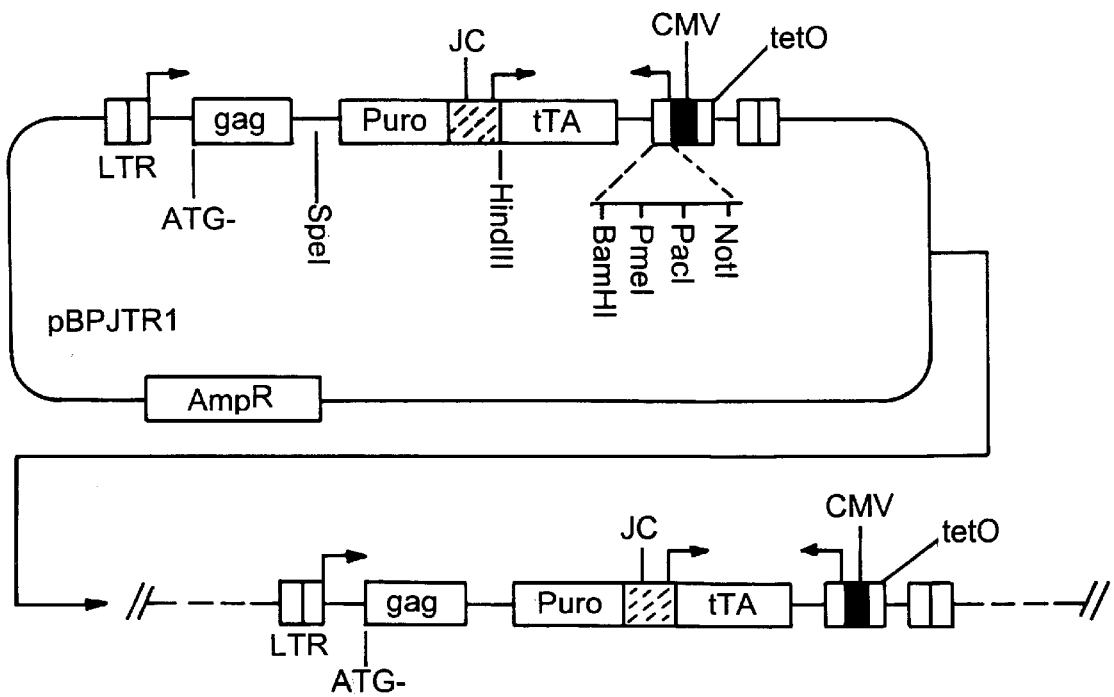

In one strategy the response unit was cloned into a ClaI site, located immediately downstream of the 3' end of the regulator unit, in an opposite orientation to the tTA-containing regulator unit (FIGS. 1*a,b*; pBPSTR1 and pBPJTR1). In this orientation, expression of the coding strand of a gene within the response unit can only be directed from the response unit promoter (tetO/minimal CMV) and not from the promoters in the regulator unit or viral 5'-LTR. Another advantage of inserting the response unit in this antisense orientation is that, in principal, a small amount of transcript produced due to potential low level leakiness of the response unit promoter should form RNA duplexes with the vast excess of transcripts originating from the constitutively active promoters within the regulator unit and 5'-LTR.

Figure 1C:
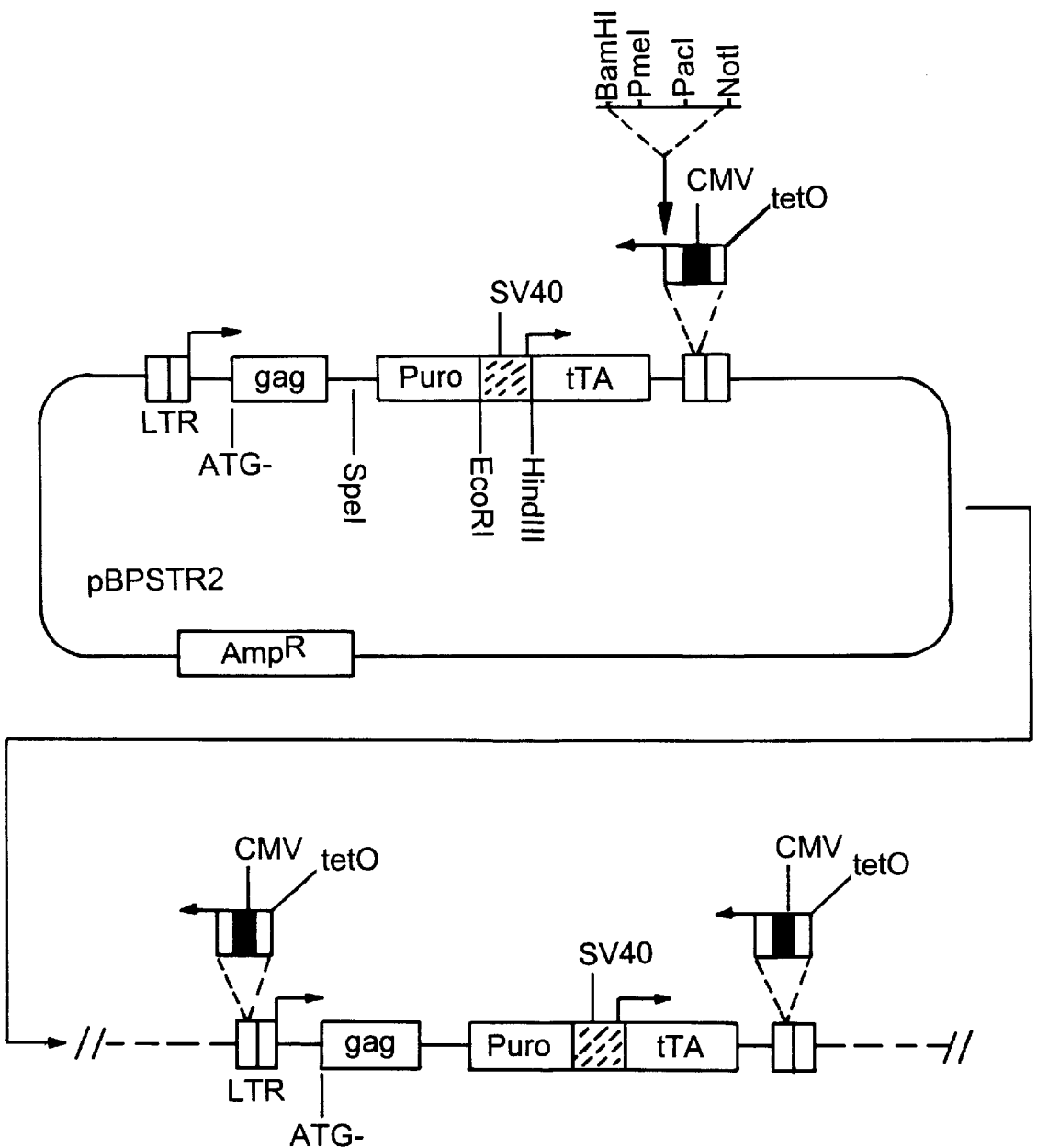
Figure 1D:
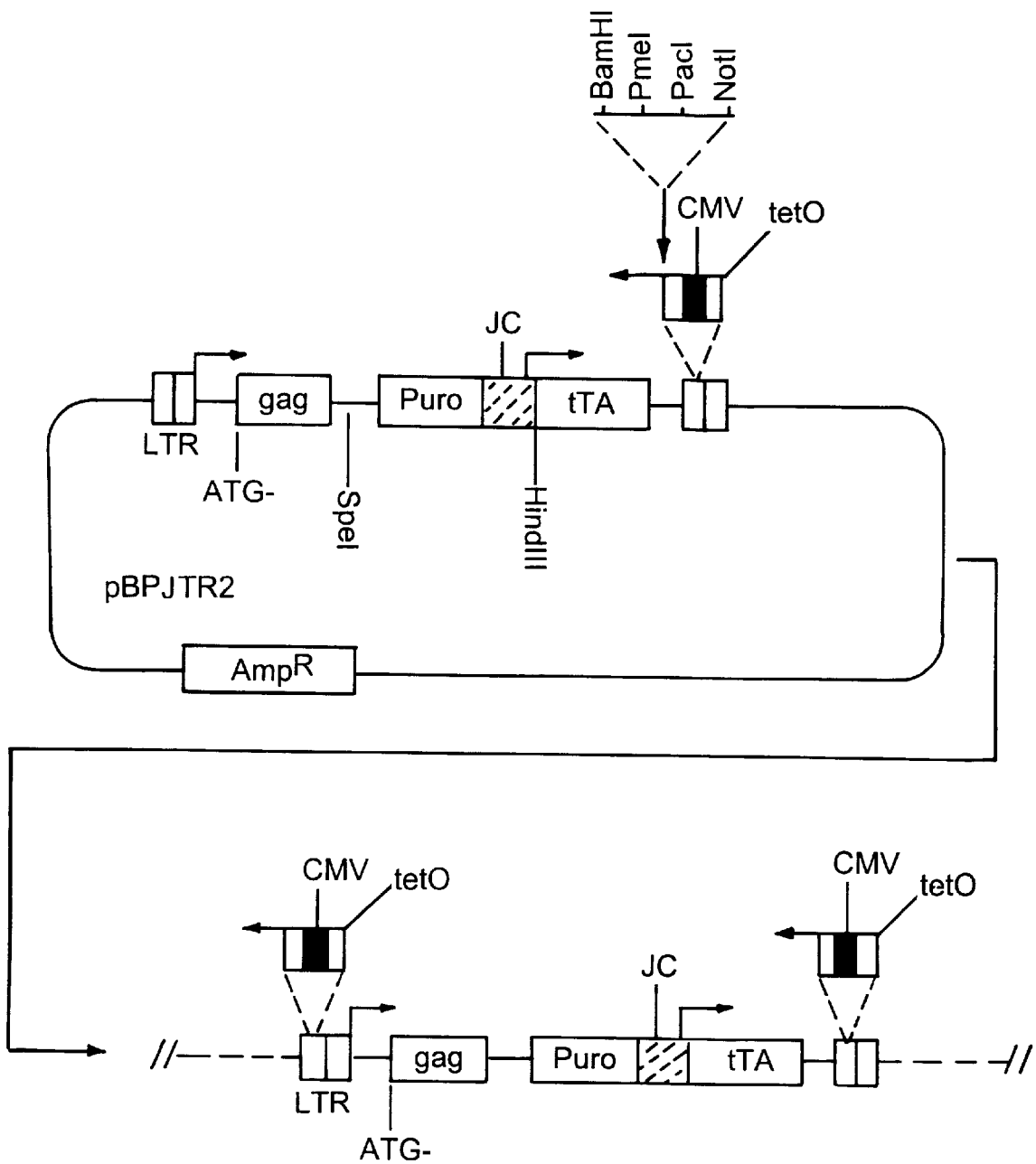

A second strategy was to clone the response unit into a BgIII site within the U3 region of the 3'-LTR (FIGS. 1*c,d*, pBPSTR2 and pBPJTR2), again in the antisense orientation relative to the regulator unit. These vectors are considered "double copy" vectors (Hantzopoulos, P.A., Sullenger, B. A., G., U. & Gilboz, E. (1989) *Proc. Natl. Acad. Sci. USA*. 86, 3519–3523), because during replication and integration of the retrovirus, the viral 3'-LTR is duplicated and replaces the viral 5'-LTR that is present in the plasmid form of the vector.

Thus, after replication and integration, any gene cloned into the U3 region of the 3'-LTR will ultimately be located 5' to the promoter within the U5 region of the LTRs. The logic for this cloning strategy is that a gene regulated by the tetO/minimal CMV promoter unit will not be transcribed by the promoters within the viral 5'-LTR or regulator unit (see FIGS. 1*c, d*).

B. Regulation of Luciferase Activity Using Single-Copy Versus Double-Copy Vectors and Different Packaging Conditions Using NIH 3T3 cells as target cells, tetracycline-dependent regulation of luciferase activity was observed for all retroviral constructs. Variability in the regulation of luciferase activity was observed depending on (1) whether tetracycline was present during packaging of the retrovirus in BOSC23 cells and (2) the organization of the components of the Tet system within the vectors (Table 1). When pBPSTluc1 virus were packaged in BOSC23 cells either in the presence (1 ug/ml) or absence of tetracycline, and then used to infect NIH 3T3 cells plated either in the presence (1 ug/ml) or absence of tetracycline, luciferase activity was 321-fold or 179-fold lower than in the absence of tetracycline. This vector thus allows efficient transfer of the components of the Tet system into target cells, including stringent repression of gene expression by tetracycline and >100-fold differences between ON and OFF states (Table 1).

To examine whether the presence of one or two copies of the response gene within the provirus affects regulation, luciferase activity was compared in NIH 3T3 cells infected with either the single-copy vector pBPSTluc1 or the double-copy vector pBPSTluc2. When tetracycline was present during the packaging of retroviral constructs in BOSC23 cells, but absent during infection of NIH 3T3 cells, luciferase activity with the single-copy vector was about 4-fold higher than that obtained with the double-copy vector (Table 1). When tetracycline was present during infection of NIH 3T3 cells, repression of luciferase activity appeared similar for both the single-copy and double-copy vectors; however, taking into account the induced activity in the double-copy vector is about 4-fold lower than the single-copy vector and that there is a corresponding increase in repressed activity as induced activity increases (for example, compare values for NIH 3T3 cells infected with pBPSTluc1 in Tables 1 and 2), the true magnitude of repressed luciferase activity in the double-copy vector should also be correspondingly 4-fold higher.

Tetracycline-dependent regulation of luciferase activity after packaging in the presence of tetracycline was 321-fold with the single-copy vector, but only 49-fold with the double-copy vector. When tetracycline was absent during packaging of retrovirus, regulation appeared to be lower, but single-copy vectors still showed better regulation than double-copy vectors (179-fold versus 18-fold, Table 1). Because of the better regulation of the Tet system observed with virus that had been packaged in BOSC23 cells in the presence of tetracycline, in all subsequent experiments we used virus packaged in this manner.

C. Regulation of Luciferase Activity by Different Internal Promoters Controlling tTA Expression To examine whether cell type-specific expression could be introduced into the Tet system-containing retroviral vectors, the glial specific JC virus early promoter was used to control expression of the tTA gene, in order to evaluate whether luciferase activity could be restricted to cells of glial origin.

pBPSTluc1 or pBPJTluc1 retrovirus were used to infect cell lines derived from different tissue origins: NIH 3T3, mouse fibroblasts; C6, rat glioblastoma; H56, rat hepatoma and Pam212, mouse squamous carcinoma. In glial derived C6 cells infected with the pBPJTluc1 retrovirus, induced luciferase activity was higher than the activity observed with the pBPSTluc1 retrovirus (FIG. 2, Table 2). In contrast, in all non-glial cell types, induced luciferase activities were higher when using the pBPSTluc1 virus than the luciferase activity observed when using the pBPJTluc1 virus (FIG. 2, Table 2).

Regulation and induced luciferase activity were generally higher in the mouse cell lines (NIH 3T3, Pam212) than in the rat cell lines (C6, H56), probably due to higher infectability of the mouse cells with ecotropic virus (FIG. 2, Table 2). The highest tetracycline-dependent regulation was observed in NIH 3T3 cells with an induction of 336-fold (regulation of the other cell types varied from 11 to 127-fold).

D. Viral Titers

In transient packaging reactions using the BOSC93 cells, the single-copy vector pBPSTluc1 produced about ten-fold higher viral titers than the double-copy vector pBPSTluc2 (Table 1). To examine whether transcriptional interference occurs in the retroviral vectors due to the placement of transcriptional units in opposing orientations to each other, BOSC23 cells were grown in the presence or absence of tetracycline during packaging of pBPSTluc1 and pBPSTluc2 constructs. Because tetracycline causes tTA to dissociate from tetO sequences and thereby inhibiting transcription of the response unit, the presence of tetracycline may facilitate the production of genomic transcripts and increase the number of viral particles. However, the titer did not significantly increase after packaging in the presence of tetracycline (Table 1). No differences in the viral titer were observed between the pBPSTluc1 and pBPJTluc1 virus or pBPSTluc2 and pBPJTluc2 (data not shown).

III. Summary

A tetracycline regulated retroviral vectors was designed and constructed to contain the tetracycline inducible Tet system. The two components of the Tet system were organized within the vectors in a manner that stringently maintains tetracycline-dependent regulation. Regulated expression of an indicator gene inserted into the retroviral vectors was examined in several different cell types. In infected NIH 3T3 cells, levels of induction in the absence of tetracycline were observed to be as high as 336-fold over levels in the presence of tetracycline, which were extremely low. Tetracycline dependent regulation was observed in all other transduced cell types and ranged from 24 to 127-fold. The generation of retroviral vectors containing regulatory elements that allow for the regulated expression of heterologous genes and that have the ability to infect virtually all dividing target cells should greatly facilitate the biochemical and genetic examination of a broad range of genes.

One novel feature of the retroviral vectors are that the Tet system was organized within a retroviral vector so that high levels of constitutively produced tTA mRNA function not only for production of tTA protein, but also to decrease basal expression of the response unit by apparent antisense inhibition. This antisense inhibition is evident when comparing tetracycline dependent regulation of the single and double copy vectors. For example, in NIH 3T3 cells, a 321-fold induction of luciferase activity was observed in the single copy vector pBPSTlucI where as a 49-fold induction was observed in the double copy vector pBPSTluc2. The lower induction value observed for the double copy vector is due to higher basal expression in the OFF state (plus tetracycline) and lower induced expression in the ON state (minus tetracycline) compared to activities observed for the single copy vector. Although basal expression of the response unit within the 3'-LTR of the double copy vector is subject to antisense inhibition, the response unit within the 5'-LTR is not. Thus, the higher basal expression observed in the double copy vector is from the response unit within the 5'-LTR. The true magnitude of the antisense effect in the single copy vector is probably higher than the data shown in Table 1, because of the lower titers of the double copy vector. The basal luciferase activity of the single copy vector is therefore much lower than that expected on the basis of gene dosage, which is probably the consequence of antisense inhibition. Interestingly, although it would be expected that antisense inhibition would also occur when transcription in the response unit is activated with tTA binding, this apparently is not a problem since relatively high levels of luciferase activity are detectable in the ON state.

TABLE 1

Regulated expression of luciferase in NIH 3T3 cells using retroviral vectors with self-contained tetracycline-dependent inducible elements

| Vector | Tet During Packaging | Tet During Infection | Luciferas Activity | Fold Induction | Titer (CFU/ml) |
|---|---|---|---|---|---|
| pBPSTluc1 | + | − | 91,082 | | |
| pBPSTluc1 | + | + | 284 | 321 | $2.1 \times 10^5$ |
| pBPSTluc1 | − | − | 83,671 | | |
| pBPSTluc1 | − | + | 467 | 179 | $1.3 \times 10^5$ |
| pBPSTluc2 | + | − | 21,412 | | |
| pBPSTluc2 | + | + | 434 | 49 | $2.7 \times 10^4$ |

TABLE 1-continued

Regulated expression of luciferase in NIH 3T3 cells using retroviral vectors with self-contained tetracycline-dependent inducible elements

| Vector | Tet During Packaging | Tet During Infection | Luciferas Activity | Fold Induction | Titer (CFU/ml) |
|---|---|---|---|---|---|
| pBPSTluc2 | − | − | 21,530 | | |
| pBPSTluc2 | − | + | 1,174 | 18 | $2.4 \times 10^4$ |

Retroviral vectors, pBPSTluc1 and pBPSTluc2 containing the luciferase gene under the transcriptional control of the tetracycline responsive transactivator (tTA) were transiently transfected into BOSC23 packaging cells (two days). Tetracycline was present (+) or absent (−) during packaging. Packaged retroviral particles were used to infect target NIH 3T3 cells. NIH 3T3 cells were plated in the presence or absence of tetracycline for measurement of inducible luciferase activity. Luciferase activity is expressed as relative light units per mg total protein cell lysate. Fold induction is the ratio −/+ tetracycline. Experiments were performed in duplicate and confirmed in additional experiments performed in an identical manner. Serial dilutions of media from packaging cells were used for titering of virus on NIH 3T3 cells. Infected cells were placed under puromycin selection and resistant colonies were counted.

TABLE 2

Regulated expression of luciferase in different cell types using retroviral vectors with self-contained tetracycline-dependent inducible elements

| Cell Type | Vector | Tet During Infection | Luciferas Activity | Fold Induction |
|---|---|---|---|---|
| NIH 3T3 | pBPSTluc1 | − | 263,190 | |
| " | pBPSTluc1 | + | 784 | 336 |
| " | pBPJTluc1 | − | 91,714 | |
| " | pBPJTluc1 | + | 669 | 137 |
| C6 | pBPSTluc1 | − | 66,347 | |
| " | pBPSTluc1 | + | 2,787 | 24 |
| " | pBPJTluc1 | − | 76,713 | |
| " | pBPJTluc1 | + | 2,271 | 34 |
| H56 | pBPSTluc1 | − | 86,970 | |
| " | pBPSTluc1 | + | 3,014 | 29 |
| " | pBPJTluc1 | − | 25,783 | |
| " | pBPJTluc1 | + | 2,267 | 11 |
| Pam212 | pBPSTluc1 | − | 512,346 | |
| " | pBPSTluc1 | + | 4,039 | 127 |
| " | pBPJTluc1 | − | 201,830 | |
| " | pBPJTluc1 | + | 5,490 | 37 |

Retroviral vectors containing the luciferase gene under the transcriptional control of the tetracycline-responsive transactivator (tTA) were transiently transfected into BOSC23 cells and packaged in the presence of tetracycline. tTa is under control of the SV40 promoter in pBPSTluc1 or the JC promoter in pBPJTluc1. Packaged retroviral particles were used to infect NIH 3T3 fibroblasts, C6 glioma cells, H56 hepatoma cells and Pam212 squamous carcinoma cells. During and after infection, NIH 3T3 cells were plated in the presence (+) or absence (−) of tetracycline for measurement of regulatable luciferase activity. Luciferase activity is expressed as relative light units per mg protein cell lysate. Fold induction is the ratio of luciferase activity −/+ tetracycline. Experiments were performed in duplicate and confirmed in additional experiments performed in an identical manner.

EXAMPLE 2

Drug Regulated Apoptotic Death in a Rat Glioma Model Mediated by a Novel Retroviral Vector This Example demonstrates in vivo efficacy of the tetracycline regulated retroviral vector. In this Example, a murine ICE-lacZ fusion gene was introduced into a novel retroviral vector designed to achieve regulated ectopic expression of a foreign gene in mammalian cells.

I. Introduction

IL-1B-converting enzyme (ICE) is a member of a growing family of cysteine proteases shown to be a crucial component in the activation of a genetic program that leads to autonomous cell death in mammalian cells. ICE is a cysteine protease that processes pro-IL-1B to an active form (Cerretti, D. P., et al. Molecular cloning of the interleukin-1 beta converting enzyme. *Science.* 256:97–100 (1992); Thornberry, N. A., et al. A novel heterodimeric cysteine protease is required for interleukin-1 beta processing in monocytes. *Nature.* 356:768–74 (1992). ICE is a mammalian homolog of the *C. elegans* cell death gene, ced-3 (Yuan, J., Shaham, S., Ledoux, S., Ellis, H. M., & Horvitz, H. R. The *C. elegans* cell death gene ced-3 encodes a protein similar to mammalian interleukin-1 beta-converting enzyme. *Cell.* 75:641–52 (1993)) and its over expression induces programmed cell death in Rat-1 fibroblasts (Miura, M., Zhu, H., Rotello, R., Hartwieg, E. A., & Yuan, J. Induction of apoptosis in fibroblasts by IL-1 beta-converting enzyme, a mammalian homolog of the *C. elegans* cell death gene ced-3. *Cell.* 75:653–60 (1993). Therapies that restore the ability to undergo programmed cell death may be of considerable benefit in some malignancies (Thompson, C. B. Apoptosis in the pathogenesis and treatment of disease. *Science*, 267:1456–62 (1995).

Initiation of programmed cell death as a means of tumoricidal therapy for gliomas was studied by delivering the ICE gene under the control of a drug regulated promoter in a retroviral vector. This approach initiates a physiologic cascade of events that leads to apoptosis. The novel drug regulated retroviral vector, as described in Example 1, allows precise control of the expression of this cell death gene. By killing glioma cells through a genetic mechanism, this strategy avoids the cytotoxicity and lack of specificity of ionizing radiation and chemotherapeutic agents, both of which have not significantly altered the natural history of this disease (Loeffler, J. S. Radiotherapy in managing malignant gliomas: current role and future directions. *Advances in Oncology.* 8:14–20 (1992); Kyritsis, A. P. & Levin, V. A. Chemotherapeutic approaches to the treatment of malignant gliomas. *Advances in Oncology*, 8:9–13 (1992).

To achieve tight control of expression of a programmed cell death gene, an ICE-lacZ fusion gene, which has previously been shown to cause apoptosis of cells in culture (Miura, M., Zhu, H., Rotello, R., Hartwieg, E. A., & Yuan, J. Induction of apoptosis in fibroblasts by IL-1 beta-converting enzyme, a mammalian homolog of the *C. elegans* cell death gene ced-3. *Cell.* 75:653–60 (1993), was introduced into a novel drug regulated retroviral vector (Paulus, W., Baur, 1., Boyce, F. M., Breakefield, X. O., & Reeves, S. A. Self contained, tetracycline regulated retroviral vector system for gene delivery to mammalian cells. *J Virol.* In press). The ICE-lacZ fusion gene corresponded to the biologically active form of the murine ICE protein (consisting of the P20 and P10 subunits) and the *E. coli* lacZ gene (Miura, M., Zhu, H., Rotello, R., Hartwieg, E. A., & Yuan, J. Induction of apoptosis in fibroblasts by IL-1 beta-converting enzyme, a mammalian homolog of the *C. elegans* cell death gene ced-3. *Cell.* 75:653–60 (1993). The tetracycline-responsive promoter allows for inhibition of transcription of the ICE-lacZ fusion gene in the presence of drug, but allows transcription to proceed in the absence of the drug (Gossen, M. & Bujard, H. Tight control of gene expression in mammalian cells by tetracycline-responsive promoters. *Proc Natl. Acad. Sci. USA.* 89:5547–51 (1992)).

II. Methods Used

A. Construction of Drug Regulated Recombinant Retrovirus

The tetracycline regulated aspect of the retroviral vector is conferred by the response and regulator units of the previously described tetracycline inducible promoter system (Gossen, M. & Bujard, H. Tight control of gene expression in mammalian cells by tetracycline-responsive promoters. *Proc Natl Acad Sci USA.* 89 5547–51 (1992)). The retroviral vector backbone is a modified version of the Moloney murine leukemia virus-based pBABE vector (Morgenstern, J. P. & Land, H. Advanced mammalian gene transfer: high titre retroviral vectors with multiple drug selection markers and a complementary helper-free packaging cell line. *Nucleic Acids Res.* 18:3587–96 (1990)) and contains the puromycin resistance gene (Puro) under the control of the promoter within the 5'-LTR. A full description of the construction of the tetracycline regulated retroviral vector is described elsewhere (Paulus, W., Baur, 1., Boyce, F. M., Breakefield, X. O., & Reeves, S. A. Self contained, tetracycline regulated retroviral vector system for gene delivery to mammalian cells. *J Virol.* in press). The regulator unit encodes a transactivator hybrid protein (tTA) constitutively driven by the SV40 promoter. The murine ICE-lacZ fusion gene was excised from BSM10Z4. This plasmid was digested with XhoI and filled-in by T4 DNA polymerase, then digested with NotI, and this fragment was cloned into the NotI-PmeI sites in the polylinker of the retroviral vector pBSTR-19. Inserting the ICE-lacZ fusion gene within the response unit in this manner places the gene under the transcriptional control of *E. coli*-derived tetracycline resistance operon regulatory elements (tetO) embedded within a minimal CMV promoter (minCMV). To construct the control lacZ retrovirus, a HindIII/EcoRI fragment was excised from pactβgal' and filled-in with T4 DNA polymerase in the presence of deoxynucleotide triphosphates (dNTPs) and then cloned into the PmeI site of pBSTR-1.

B. Cell Culture

The drug regulated retroviral vector containing the ICE-lacZ gene was transfected into BOSC23 packaging cells in the presence of tetracycline to produce infectious retrovirus as described (Pear, W. S., Nolan, G. P., Scott, M. L., & Baltimore, D. Production of high titer helper-free retroviruses by transient transfection. *Proc Natl Acad Sci USA.* 90, 8392–6 (1993)). Rat 9L gliosarcoma cells (ATCC) were then infected with the supernatant containing retrovirus and cloned under puromycin selection (5 μg/ml) in the presence of tetracycline (1 μg/ml) for approximately 10 days. A puromycin-resistant clone that expressed a high amount of ICE-lacZ in the absence of tetracycline, designated 9L-ICE-lacZ, was further characterized.

C. B-Galactosidase Assay

9L-ICE-lacZ was characterized for the induction of the ICE-lacZ gene using a B-galactosidase assay which measures the amount of the substrate ONPG (o-nitrophenyl-B-D-galactopyranoside) that is hydrolyzed to onitrophenol by absorbance at 420 nm (Promega). 9L-ICE-lacZ cells were seeded at a density of 2×105/well in 6-well dishes and grown in media (Dulbecco's modified Eagle's medium with 10% fetal calf serum) containing tetracycline (1 μg/ml). The next day, cells were washed and placed in media with or without tetracycline (1 μg/ml). Cells grown in the presence or absence of tetracycline for 12 and 24 hours were harvested and assayed for B-galactosidase activity and total protein content (Bradford assay). Experiments were done in triplicate and all assays were performed in duplicate.

D. Histological Analysis of B-galactosidase Expression

Cells were seeded at a density of $2 \times 10^5$/well in 6-well dishes. After 24 hours in the presence or absence of tetracycline, expression of ICE-lacZ in 9L-ICE-lacZ cells or lacZ in 9L-lacZ cells, was determined by fixing the cells with 0.5% glutaraldehyde for 10 min, rinsing three times with phosphate-buffered saline (PBS), and staining in X-gal buffer (1 mg/ml 5-bromo-4-chloro-3-indoxyl B-galactoside, 5 mM $K_3Fe(CN)6$, 5 mM $K_4Fe(CN)_6$-$3H_2O$, 2 mM $MgCl_2$ in 0.1 M sodium phosphate buffer (pH 7.4) at 37° C. for 12 hours (Price, J., Turner, D., & Cepko, C. Lineage analysis in the vertebrate nervous system by retrovirus-mediated gene transfer. *Proc. Natl. Acad. Sci. U.S.A.* 84:156–160 (1987)).

E. Viability Assay

9L-ICE-lacZ cells were grown on coverslips and 24 hours after ICE-lacZ induction by removal of tetracycline, culture medium was replaced with 1 μM calcein-AM and 10 μg/ml propidium iodide in PBS for 20 min at 37° C. Viable cells cleave calcein-AM to calcein, producing green fluorescence, whereas dead cells take up propidium iodide into the nucleus, resulting in intense red fluorescence. Green and red fluorescence were simultaneously visualized using a Nikon transmission microscope (Asai, A., et al. Negative effects of wild-type p53 and c-Myc on cellular growth and tumorigenicity of glioma cells. Implication of the tumor suppressor genes for gene therapy. *J. Neuro-Oncol.* 19, 259–268 (1994); Louis, D. N. The p53 gene and protein in human brain tumors. *J. Neuropath. and Exper. Neurol.* 53, 11–21 (1994)). Three 0.8 $mm^2$ fields were counted for each 50 mm well. All wells were counted in triplicate and over 300 cells were scored per well. Percents of dead red cells relative to all cells F. Hoescht Stain 9L-ICE-lacZ cells grown on cover slips were prefixed with 4% paraformaldehyde and washed in PBS, incubated with Hoescht 33258 dye (final concentration, 5 μM) for 1 min, washed again in PBS, and examined with a Zeiss Axiophot fluorescence microscope.

G. 9L-ICE-lacz Expression in Intracranial Rat Glioma Model

12 Male CD Fisher rats weighing approximately 300 g (Charles River) were administered tetracycline (1.0 mg/ml) in their drinking water as described (Fishman, G. J., Kaplan, M. L., & Buttrick, P. M. Tetracycline regulated cardiac gene expression in vivo. *J Clin Invest.* 93:1864–8 (1994)). Four days later, animals were anesthetized with ketamine/xylazine (1/1) and $2 \times 10^5$ 9L-ICE-lacZ cells were stereotactically implanted in the right striatum. The implantation procedure was essentially as described previously (Kobayashk N., AHen, N., Clendenon, N.Rv & Ko, L. W. An improved rat brain-tumor model. *J Neurosurg.* 53:808–15 0980)). Eight animals were taken off tetracycline 7 days later and sacrificed at 2, 4, 6, and 9 days post removal of tetracycline and perfused with 4% paraformaldehyde, sectioned, and stained for X-gal histochemistry as described above and counterstained with neutral red. Comparable time point 9L-ICE-lacZ tumor-bearing animals maintained on tetracycline were sacrificed in parallel with the animals that had been taken off tetracycline. In situ DNA end-labeling was performed on frozen brain sections of 9L-ICE-lacZ tumor-bearing animals on or off tetracycline for 4 or 9 days. Internucleosomal DNA fragmentation was detected by horseradish peroxidasedigoxigenin nucleotide labeling of 3'-OH DNA ends (Apoptag, Oncor). All animal studies were done in accordance with guidelines for animal care by the Massachusetts General Hospital Subcommittee on Animal Care.

H. Subcutaneous Growth of 9L-ICE-lacZ Tumor on and off Tetracycline

Eight animals were given tetracycline in their drinking water for 4 days and then $5 \times 10^5$ 9L-ICE-lacZ cells in a total volume of 0.1 ml were injected subcutaneously in the right flank of each rat. Animals were maintained on tetracycline for 7 days at which point half the animals were then taken off the drug. Tumor volumes were determined at two day intervals with the aid of calipers.

III. Results

A. Induction of ICE-lacZ Expression Using a Drug Regulated Retroviral Vector

Figure 3A:
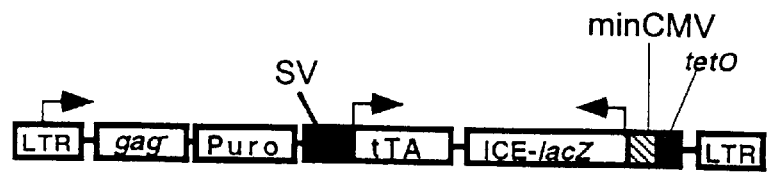

The drug regulatable aspect of the retroviral vector was introduced by including both the "response" and "regulator" units of the previously described tetracycline (Tet) inducible promoter system (Gossen, M. & Bujard, H. Tight control of gene expression in mammalian cells by tetracycline-responsive promoters. *Proc Natl Acad Sci USA*. 89:5547–51 (1992)) into the backbone of a MoMLV-derived retrovirus vector (FIG. 3A). FIG. 3 (A) is a diagram of the ICE-lacZ-containing tetracycline regulated retroviral vector used in the experiments. The puromycin resistance gene (Puro) is under the control of the promoter within the 5'-LTR. The murine ICE-lacZ fusion gene is cloned into the response unit and is under the transcriptional control of *E. coli*-derived tetracycline resistance operon regulatory elements (tetO) embedded within a minimal CMV promoter (minCMV). The regulator unit encodes a transactivator hybrid protein (tTA) composed of the tetracycline repressor (tetR) fused to the herpes simplex virus transactivator protein, VP16, and is under the transcriptional control of the constitutively active SV40 promoter (SV). In the absence of tetracycline, tTA protein binds tetO sequences within the response unit via its tetR domain and activates transcription of the ICE-lacZ gene. In the presence of tetracycline, which binds tTA, tTA dissociates from the response unit and transcription of the ICE-lacZ gene is inhibited. Arrows indicate the direction of transcription.

Extremely low levels of basal expression from the response unit in the presence of tetracycline were accomplished (Paulus, W., Baur, l., Boyce, F. M., Breakefield, X. O., & Reeves, S. A. Self contained, tetracycline regulated retroviral vector system for gene delivery to mammalian cells. *J Virol.* in press) by placing the response and regulator units of the Tet inducible system in an antisense configuration (FIG. 3A).

Figure 3B:
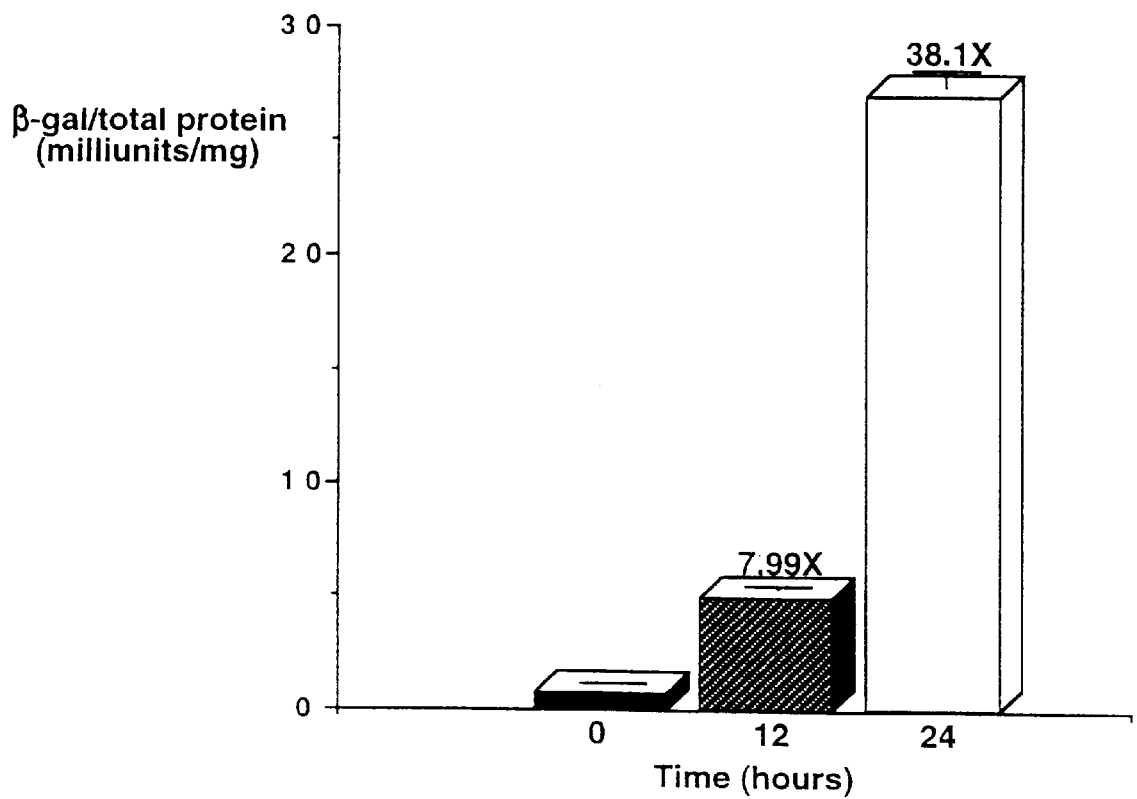

Rat 9L gliosarcoma cells were infected with the retroviral vector containing-the ICE-lacZ gene and cloned under puromycin selection in the continued presence of tetracycline. Multiple 9L puromycin-resistant clones were isolated and one of the clones, that stained intensely with X-gal when tetracycline was removed, was designated 9L-ICE-lacZ and further characterized for tetracycline-dependent expression of the ICE-lacZ gene. Using an B-galactosidase enzyme assay, induction of ICE-lacZ gene expression in this 9L-derived clone was 7.99-fold and 38.1-fold, 12 hours and 24 hours, respectively, after removal of tetracycline (FIG. 3B).

B. Regulated Expression of ICE-lacZ Induces Apoptosis in Cultured Glioma Cells

Figures 4A, 4B, 4C:
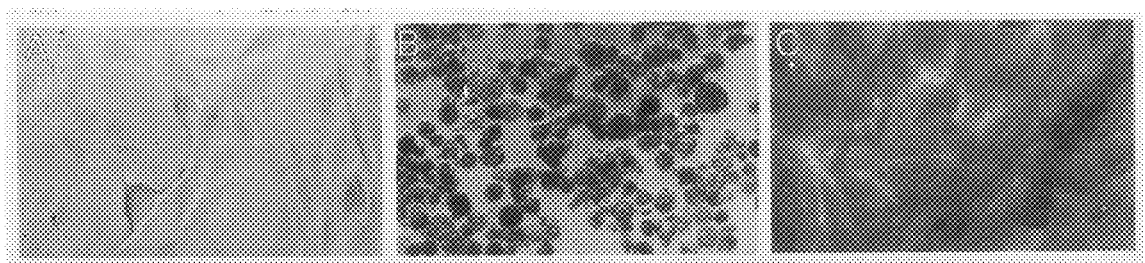

9L-ICE-lacZ cells grown in the presence of tetracycline did not stain blue with X-gal and exhibited normal morphology (FIG. 4A). In contrast, X-gal staining of 9L-ICE-lacZ cells 24 hours after removal of tetracycline demonstrated that all cells stained blue, and thus were expressing the ICE-lacZ gene (FIG. 4B). In addition to blue staining, all cells exhibited typical morphologic features of apoptosis, including cell shrinkage, membrane blebbing, and apoptotic bodies (FIG. 4B). A clone of 9L cells, 9L-lacZ, infected with a control vector containing the lacZ gene under the same tetracycline-dependent promoter stained blue without any apoptotic features in the absence of tetracycline (FIG. 4C).

Figures 4D, 4E, 4F:
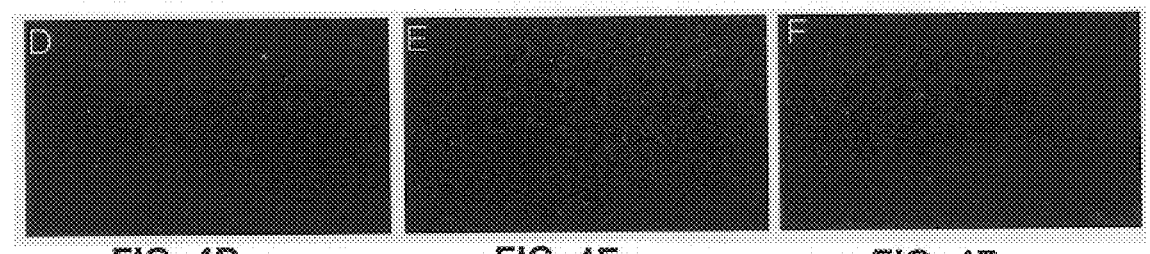
Figures 4G, 4H:
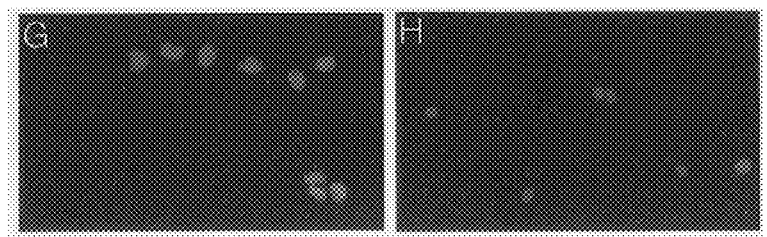

Cell viability was assessed by a calcein-AM/propidium iodide double-fluorescence assay. Viable 9L-ICE-lacZ cells grown in the presence of tetracycline exhibited green cytoplasmic fluorescence (FIG. 4D), while dead cells taken off tetracycline for 24 hours exhibited red nuclear fluorescence (FIG. 4E). Propidium iodide fluorescence revealed a characteristic nuclear blebbing pattern in all cells when tetracycline had been removed for 24 hours (FIG. 4F). Ultraviolet absorption after Hoechst staining of cells on tetracycline exhibited large, normal nuclei (FIG. 4G), whereas cells off tetracycline exhibited chromatin condensation and apoptotic morphology in their nuclei (FIG. 4H).

Figure 4I:
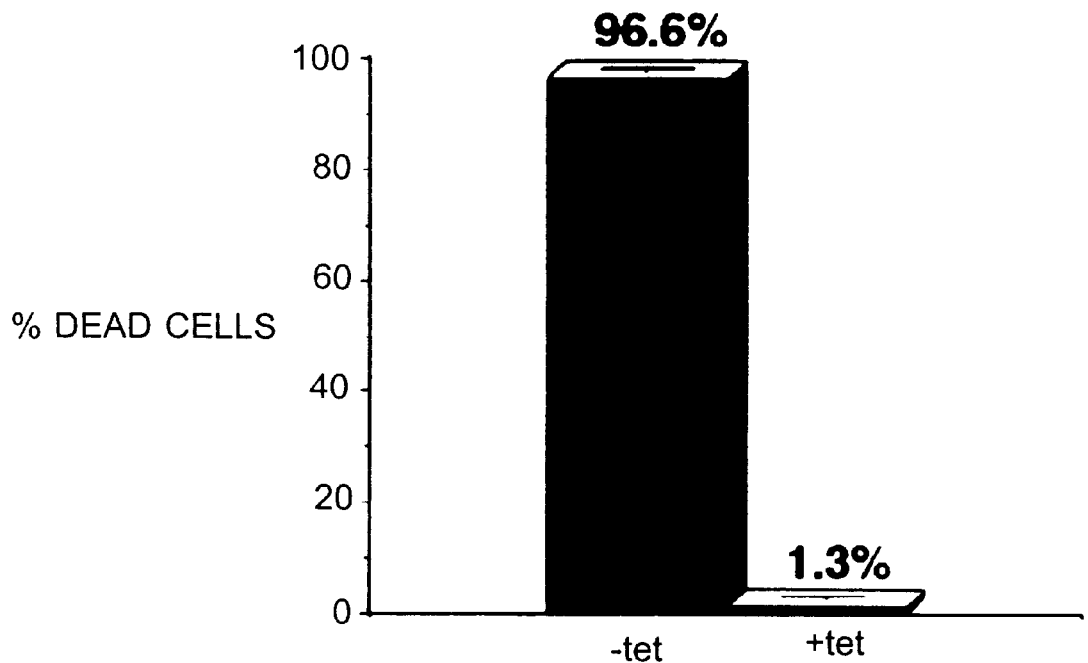

In the absence of tetracycline for 24 hours, 96.6% of cells had undergone programmed cell death while only 1.3% of cells were dead in a parallel culture maintained with tetracycline (FIG. 4I).

Figure 5H:
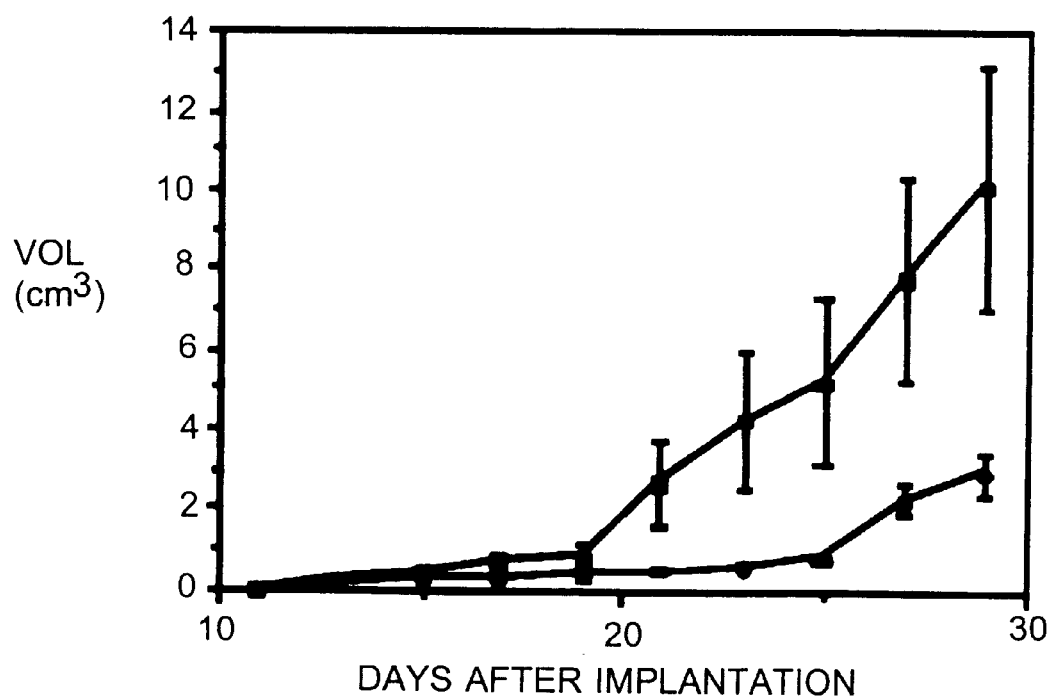
Figures 5A, 5B:
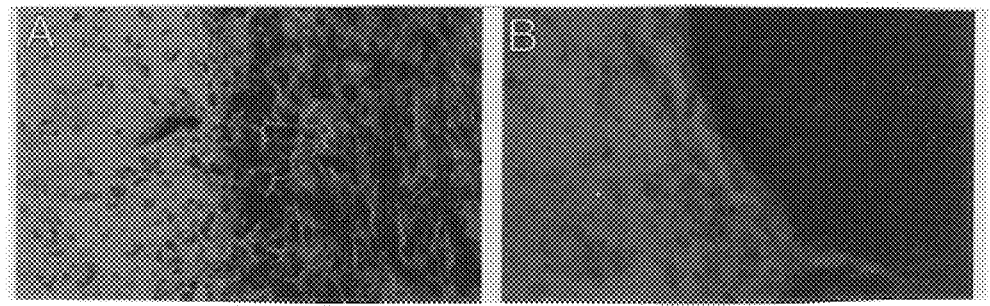

C. Regulated Expression of ICE-lacZ Induces Apoptosis In an Intracranial Glioma Model To determine whether control of ICE expression and induction of apoptosis could be achieved in vivo, 9L-ICE-lacZ cells were implanted in the right striatum of rats that had been on tetracycline for 4 days. To allow initial growth of the implanted tumor cells, animals were given tetracycline hydrochloride for 7 days in their drinking water. The animals were then divided into two groups; in one group, tetracycline was retained in their drinking water, while in the other group, tetracycline was removed. Animals from both groups were then sacrificed at 2, 4, 6, and 9 days after removal of tetracycline. Animals at 2 days after removal of tetracycline showed X-gal staining particularly in tumor cells adjacent to normal brain with rounded blue cells reminiscent of the condensed cytoplasm associated with apoptosis (FIG. 5A). Animals of a comparable time point maintained on tetracycline bore tumors without X-gal staining, demonstrating that tetracycline efficiently repressed expression of the ICE-lacZ gene in vivo (FIG. 5B).

Figures 5C, 5D:
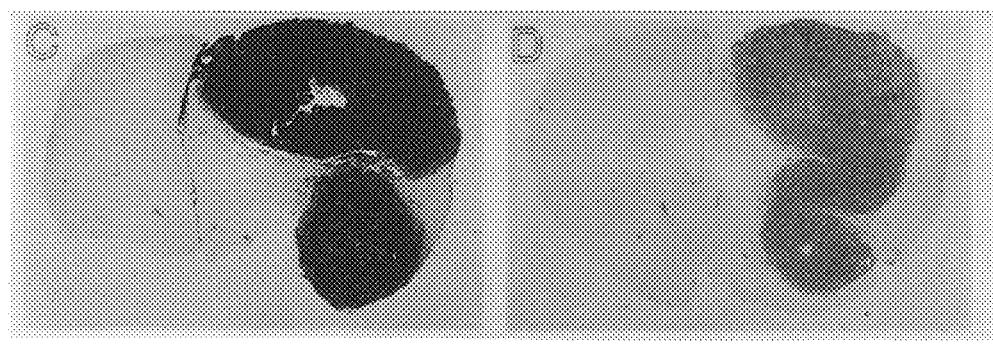
Figures 5E, 5F:
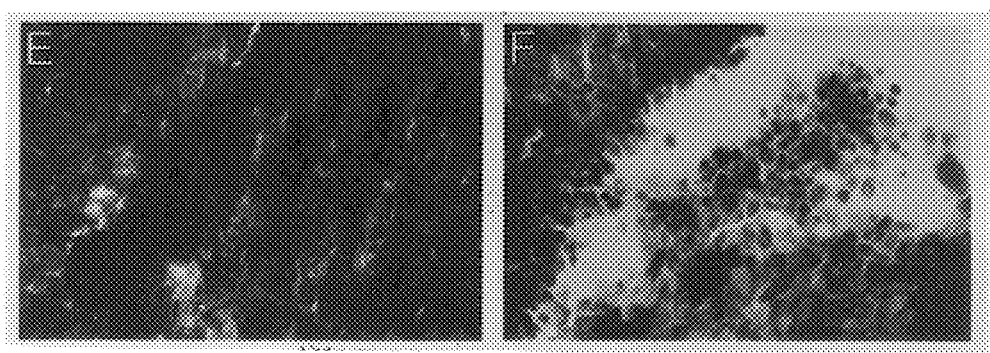
Figure 5G:
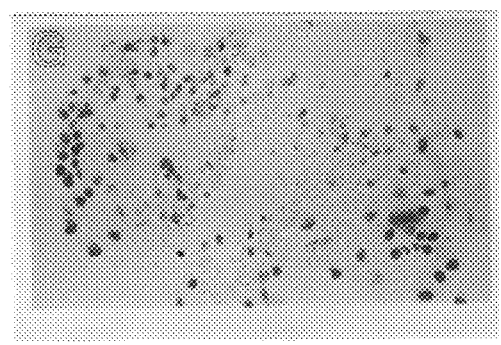

By 4 days after removal of tetracycline, the entire tumor, except for endothelial cells, expressed the ICE-lacZ gene, as demonstrated by intense X-gal staining (FIG. 5C). In contrast, in a comparable time point animal maintained on tetracycline, repression of the ICE-lacZ gene was still clearly in effect, since no X-gal staining was evident at this time (FIG. 5D). In animals taken off tetracycline for 4 days, there were numerous areas of cell death The most intense region of cell death was within the central part of the tumor with smaller areas of cell death radiating out toward the peripheral areas of the tumor. The neutral red counterstain revealed areas of nuclear heterogeneity and morphology suggestive of the nuclear condensation associated with apoptotic cell death in a background of X-gal positive staining (FIG. 5E). There were also, in some areas, shrunken, rounded up cells that had detached from the cellular architecture consistent with apoptosis (FIG. 5F). Morphologic features of apoptosis were also noted in tumors in animals 6 and 9 days after removal of tetracycline (data not shown).

One animal, in which tetracycline was retained in its drinking water for 9 days, demonstrated some X-gal positive staining in the 9L-ICE-lacZ tumor; however, this animal bore a large intracranial tumor and may have been too lethargic to drink sufficient tetracycline water to keep the gene off. In situ DNA end-labeling revealed internucleosomal DNA fragmentation in condensed and fragmented nuclei in areas of tumor cell death in animals off tetracycline for 4 and 9 days (FIG. 5G), but not at comparable time points in animals maintained on tetracycline (data not shown).

D. Effect of ICE-lacZ on Tumorigenicity

In parallel with the intracranial tumor study, rats inoculated subcutaneously with 9L-ICE-lacZ cells were kept on tetracycline for 7 days, then tetracycline was removed from the drinking water of half of the animals. Subsequent measurement of tumor volumes were determined at two day intervals. The subcutaneous tumors in animals taken off tetracycline were statistically smaller in size than the tumors in animals that were kept on tetracycline (FIG. 5H).

IV. Summary

IL-1B-converting enzyme (ICE) is a member of a growing family of cysteine proteases shown to be a crucial component in the activation of a genetic program that leads to autonomous cell death in mammalian cells. In this Example a murine ICE-lacZ fusion gene was introduced into a novel retroviral vector designed to achieve regulated ectopic expression of a foreign gene in mammalian cells. By delivering the ICE-lacZ gene within a retroviral vector and under the control of a tetracycline regulated promoter, the intrinsic cell death program of ICE was used as a means for tumoricidal therapy in a rat brain tumor model. The results demonstrated that both, in culture (in vitro) and in vivo, suppression of ICE-lacZ expression was extremely tight in the presence of tetracycline, as determined by the lack of X-gal positive tumor cells and by cell viability. When tetracycline was withdrawn, ICE-lacZ gene expression was rapidly turned on and apoptosis mediated cell death (evidenced by widespread apoptosis occurred as evidenced by tumor cell cytoplasmic reduction, detachment of cells from the tumor architecture, nuclear condensation, and internucleosomal DNA fragmentation) occurred in essentially all tumor cells.

V. Potential Applications

Tumorigenesis may in part result from loss of a cell's ability to undergo apoptosis in response to physiologic stimuli (Hoffman, B. & Liebermann, D. A. Molecular controls of apoptosis: differentiation/growth arrest primary response genes, proto-oncogenes, and tumor suppressor genes as positive & negative modulators. *Oncogene*. 9, 1807–12 (1994)). By overexpressing a cell death gene that encodes a protein likely responsible for the final stages of the programmed cell death program, this program can be initiated at a relative downstream point and potentially bypass tumor cell resistance to apoptosis. Indeed, the results described in this study suggest this paradigm may be applicable in clinical situations. In this regard, the tightly regulated expression afforded by this retroviral vector in vivo allows time for gene delivery e.g. grafting of packaging cells into the tumor with infection of dividing cells (Short, M. P., et al. Gene delivery to glioma cells in rat brain by grafting of a retrovirus packaging cell line. *J Neurosci Res*. 27, 427–39 (1990)) and then for precise induction of death of both the tumor cells and packaging cells. The packaging cells are thereby allowed to migrate and infect tumor to increase gene transduction efficiency and induced to undergo cell death along with tumor to increase safety. This vector should be useful in other gene therapy paradigms where precise induction of gene expression is desirable. Both temporal and quantitative control of the expression of a gene product would augment the clinical applicability of gene therapy. Furthermore, this vector could enhance the study of the biochemical events during programmed cell death which have been elusive due to the lack of a model exhibiting synchronized progression into cell death.

Clearly there is an attraction to harnessing a potent genetic program that is already in place in vertebrates for tumoricidal therapy. Interestingly, recent studies suggest that radiation therapy, chemotherapy, and gene therapy (e.g. gangciclovir activated by herpes simplex virus thymidine kinase), whose therapeutic effect had traditionally been attributed to direct DNA damage, may exert their cytotoxic effects through a programmed cell death mechanism (Lowe, S. W., Schmitt, E. M., Smith, S. W., Osborne, B. A., & Jacks, T. p53 is required for radiation-induced apoptosis in mouse thymocytes. *Nature*. 362 847–849 (1993); Lowe, S. W., Ruley, H. E., Jacks, T., & Housman, D. E. p53-dependent apoptosis modulates the cytotoxicity of anticancer agents. *Cell*. 74 957–67 (1993); and Freeman, S. M., et al. The "bystander effect": tumor regression when a fraction of the tumor mass is genetically modified. *Cancer Res*. 53, 5274–83 (1993)).

As with many human gliomas, 9L gliosarcoma cells contain a mutant form of p53 (Asai, A., et al. Negative effects of wild-type p53 and c-Myc on cellular growth and tumorigenicity of glioma cells. Implication of the tumor suppressor genes for gene therapy. *J. Neuro-Oncol*. 19, 259–268 (1994); Louis, D. N. The p53 gene and protein in human brain tumors. *J. Neuropath. and Exper. Neurol*. 53, 11–21 (1994)). It has recently been shown that cisplatin induces ICE expression in murine and human glioma cell lines during apoptosis regardless of their p53 status (Kondo, S., Barna, B. P., Morimura, T., Takeuchi, J., & Barnett, G. H. Cisplatin induces expression of interleukin-1 beta converting enzyme in murine and human glioma cells during apoptosis regardless of their p53 status. *Annual Meeting of the Congress of Neurological Surgeons*. San Francisco, Calif. (1995)). Thus, induction of apoptosis by the ICE-lacZ protein in 9L gliosarcoma cells demonstrates that ICE function is downstream or independent of p53 function and suggests that ICE-mediated tumoricidal therapy is possible even in tumors with mutant p53. As more cell death or growth suppressive genes and their mechanism of action become elucidated, these genes may be of use in the paradigm established in this study both as therapeutic tools and as a means of studying the homeostasis of cell proliferation and death.

EXAMPLE 3

Construction of a "Reverse" Drug Regulatable Retroviral Vector

The drug regulated retroviral vector, as described in Example 1 and FIG. 6A, can be modified such that the expression of a gene cloned into the response unit of the retroviral vector is not expressed unless tetracycline is present. FIG. 6 compares the construct of the original tetracycline regulated retroviral vector (FIG. 6A) with the "reverse" tetracycline regulatable retroviral vector, designated pBPSrTR-1 (see FIG. 6B as compared to FIG. 6A). The reverse tetracycline regulatable retroviral vector is designed such that the tTA gene in pBPSTR-1 (see FIG. 6B) has been removed, altered and then replaced so that the altered tTA ["reverse" tTA (rtTA)] requires the presence of tetracycline, tetracycline derivatives or tetracycline analogues to bind promoter elements within the response unit promoter and activate the expression of the gene inserted into the response unit. This was accomplished by first excising the tTA gene from the pBSTR-1 retroviral vector with HindIII/BamH1. Next, the "reverse" rtTA gene was obtained from Dr. Bujard and the 5' and 3' ends were modified using HindIII and BamH1 adapter primers and the polymerase chain reaction (PCR) so that the adapted rtTA gene could be inserted into pBPSTR-1, to construct the retroviral vector pBPSrTR-1. In the version of the tetracycline regulatable retroviral vector as described in Example 1, expression of a gene inserted into the multiple cloning site of the response unit is dependent on tTA protein binding to tetO sequences in the response unit. The tTA protein is different than the "reverse" tTA (rtTA) protein present in the "reverse" retroviral vector (pBPSrTR-1) because it does not need to bind tetracycline for it to also bind tetO sequences and activate expression of a gene in the response unit. However, in the original vector, when tetracycline does bind tTA protein, this causes tTA to dissociated from tetO sequences and turns off expression of a gene in the response unit (See FIG. 6A).

In the reverse tetracycline regulatable retroviral vector, expression of a gene inserted into the multiple cloning site of the response unit is dependent on "reverse" tTA (rtTA) protein binding to tetO sequences in the response unit. The reverse tTA (rtTA) protein is different than the tTA protein present in the original retroviral vector (pBPSTR-1, FIG. 6A) because it needs to bind tetracycline for it to also bind tetO sequences and activate expression of a gene in the response unit (See FIG. 6B).

The applications for the "reverse" acting tetracycline-regulatable retroviral vector will be the same as those described for the original tetracycline regulatable retroviral vector, pBPSTR-1.

EXAMPLE 4

Treatment of Neurological Disorders Using a Rat Model

This Example demonstrates how a tetracycline regulated retroviral vector can be used to treat neurological disorders. TyrQsine hydroxylase (TH) is a rate-limiting enzyme necessary for the biosynthesis of dopamine and glial derived neurotrophic factor (GDNF) is a neurotrophic factor important for motor and dopaminergic neuron survival and uptake of dopamine in dopaminergic neurons.

Specifically, a retroviral vector containing tetracycline inducible promoter elements was used in these experiments which made it possible to deliver and regulate the expression of a therapeutic gene in diseased cells. In practice, expression of the TH and GDNF genes are under the transcriptional control of a tetracycline:VP16 transactivator fusion protein (tTA), which positively regulates expression of the therapeutic gene in the absence of tetracycline; however, in the presence of tetracycline expression of the TH and GDNE genes are repressed.

A tetracycline regulatable retroviral vector containing the GDNF gene and a tetracycline regulatable retroviral vector containing the TH gene was constructed as shown in FIG. 7.

Rat1 fibroblast cells were used in these experiments because they serve as excellent models for humans and can be used in a rat neurodegenerative model that mimics quite well the human disorder. To demonstrate the efficiency of retroviral delivery of the TH and GDNF genes (FIG. 7) and the tetracycline-dependent gene expression of the delivered genes, Rat1 fibroblasts were infected with retrovirus containing either the TH or GDNF gene using methods as described in Example 2. Infected puromycin-resistant Rat1 fibroblasts clones were examined for tetracycline dependent regulated expression of the GDNF (FIG. 8A, clones GD2, GD3, GD4, GD5, GD6) and TH genes (see FIG. 8B, clones TH1, TH3, TH4). Shown in FIGS. 8A and 8B are western blots of protein from puromycin resistant clones that had been selected from pools of Rat1 cells that have been infected with the tetracycline regulatable retrovirus. Clones GD2, GD3, GD4, GD5, GD6, TH1, TH3, TH4 are different Rat1 clones selected with puromycin as described in the above Examples. The "−" means that the clones were not treated with tetracycline and "+" means that the clones were treated with tetracycline). "C" is the non-infected Rat1 control cells. The results demonstrated that GDNF and TH gene expression was inhibited in tetracycline treated clones and GDNF and TH was expressed in clones not treated with tetracycline. These results demonstrate the gene delivery is very efficient and that expression of the delivered genes can be tightly controlled with tetracycline.

Also, a rat model system will be used to determine whether restoring normal levels of dopamine to the brains of 6-hydroxydopamine treated rats using the tetracycline regulated retroviral vectors of this invention can provide a curative therapy for this neurological disorder. The strategy to be used includes using rat fibroblasts (Rat1) clones that carry the TH and GDNF genes for implantation into the striatium of 6-hydroxydopamine treated rats where they should manufacture the TH and GDNF proteins while remaining externally controlled via tetracycline. This approach is advantageous because it reduces the risk of rejection of the implant by the immune system and also adds the tetracycline controlled expression component. Furthermore, the presence of GDNF should enable dopamine receptor-bearing cells to thrive and to more effectively uptake the new, higher level of dopamine resulting from TH activity.

EXAMPLE 5

Treatment of Parkinson's Disease in Humans

This Example demonstrates how a tetracycline regulated retroviral vector can be used to treat patients with Parkinson's disease.

I. General Background on Parkinson's Disease

Paralysis agitans, commonly known as Parkinson's disease, is a relatively common neurologic disorder of the brain where a specific class of dopaminergic neurons located in the nigrostriatal pathway deteriorate. The reason for this degeneration is unknown, although, oxidative damage, environmental toxins, genetic predisposition, and accelerated aging have all been proposed to be possible factors in the disease. Whichever the cause, the loss of these neurons can have a profound impact on the afflicted individual. In part, this is because dopaminergic neurons normally produce dopamine and when they degenerate, dopamine levels in the brain are substantially reduced. Dopamine is important because it functions as a chemical messenger responsible for transmitting signals between the substantia nigra and the corpus striatum of the brain to produce smooth, purposeful muscle activity. Loss or decreased levels of dopamine causes the nerve cells of the corpus striatum to fire 'out of control,' leaving patients unable to direct or control their movements in a normal manner. Symptoms of this disease include stiffness, tremor, slowness of movement, difficulty with balance, and difficulty in walking.

Drug therapy-based treatments for patients with Parkinson's disease are currently in use to replace the dopamine lost in the disease process. L-dopa (Levodopa; an intermediate in the biosynthesis of dopamine) or related agents, bring relief to many patients, but L-dopa becomes ineffective over time and debilitating side-effects develop with prolonged use. Kupsch, A. & Oertel, W. H. (1994), Life Sciences, 55:2033–2095.

A strategy involving intrastriatal implantation of human fetal dopamine-rich mesencephalic tissue has shown sustained improvement of motor function in Parkinsonian patients. Freed, C. R., Breeze, R. E., Rosenberg, N. L. Schneck, S. A., et al. (1992), New England Journal of Medicine, 327:1549–1555. However, ethical issues involving the use of abortive human fetuses as a source for dopamine-rich mesencephalic tissue has generated considerable debate.

An alternative to using fetal tissue as a source for dopamine and neurotrophic factor production is to genetically modify non-neuronal cells from the Parkinsonian patient with the capacity to produce dopamine and neurotrophic factors.

This Example demonstrates a rat parkinson model and teaches methods to genetically modify cells from the Parkinsonian patient to increase and control the production and uptake of dopamine.

II. Construction of a Tetracycline Regulated Retroviral Vector Containing the Gene Encoding Tyrosine Hydroxylase A tetracycline regulated retroviral vector containing the DNA encoding tyrosine hydroxylase (TH) was constructed by employing the methods taught in Examples 1 and 2. Tyrosine hydroxylase is a rate-limiting enzyme necessary for the biosynthesis of dopamine. Zigmond, R. E., Schwarzschild, M. A. & Rittenberg, A. R. (1989), Annu. Rev. Neurosci, 12:415–461. In this vector, the human tyrosine hydroxylase (TH) cDNA was excised from the plasmid pTH with BamH1 and cloned into the BamH1 site of pBPSTR-1 placing the TH gene under the control of the tetO/min CMV promoter in the response unit. Regulation of this enzyme with or without the presence of tetracycline, via employing a tetracycline regulated retroviral vector, allows for the controlled expression of this enzyme.

Although, other studies have used viral vectors to deliver the TH gene to cells that potentially could supply dopaminergic neurons with dopamine or L-dopa. Gage, F. H, et al (1987), Neuroscience, 23:795–807; Gage, F. H. & Fisher, L. J., et al (1991), Neuron, 6:1–12, this approach is unique in that viral gene delivery vectors contains elements that allow for tetracycline regulated expression of the delivered gene (pBPSTR-1) (Paulas, et al., J. Virology in press).

III. Construction of a Tetracycline Regulated Retroviral Vector Containing the Gene Encoding Glial-Derived Neurotrophic Factor A tetracycline regulated retroviral vector containing the DNA encoding glial-derived neurotrophic factor (GDNF) was constructed by employing the methods taught in Examples 1 and 2. GDNF is a neurotrophic factor important for motor and dopaminergic neuron survival and uptake of dopamine in dopaminergic neurons. The GDNF cDNA was excised from the plasmid pGDNF with BamH1/Not1 and cloned into the BamH1/Not1 sites of pBPSTR-1 placing the GDNF cDNA under the control of the tetO/min CMV promoter in the response unit. Lindsay, R. M. (1995), Nature, 373, 289. Regulation of GDNF with or without the addition of tetracycline, via employing a tetracycline regulated retroviral vector, allows for the controlled expression of this enzyme.

IV. Isolate and Infect Fibroblasts from Patients with Parkinson's Disease

Based on studies using rat fibroblasts isolated from rat brain and then reimplanted back into a rat parkinson model brain, brain-derived fibroblast cells are isolated from patients with Parkinson's disease. These cells will be infected with the tetracycline regulated retroviral vector containing the TH or GDNF gene as described in Sections II and III above and reimplanted back into the brain of the Parkinson patient.

Because of the design of these vectors, tyrosine hydroxylase or GDNF will be synthesized constitutively until tetracycline is administered to the patient. Thus, tetracycline can be used to control the production of tyrosine hydroxylase and GDNF in a patient with Parkinson's disease.

Thus, the tetracycline regulated retroviral vectors of this invention not only provide a means of regulating expression of a gene, e.g., TH or GDNF, in an "OFF" or "ON" manner, but also allow for controlling intermediate levels of expression. This could be important during periods when more or less amounts of the TH or GDNF are required by the Parkinson patient. The level of GDNF or TH expressed can be achieved by increasing or decreasing the pharmacological levels of tetracycline; this allows for controlling situations where greater or less dopamine is needed.

Rat1 fibroblast cells have been used in similar experiments (See Example above), and one of ordinary skill in the art knows that the rat can serve as an excellent model for humans. Thus, success in the rat model provides evidence that the same techniques using human compatible promoters, etc, will be effective in treating patients with Parkinson's disease. Other embodiments are within the following claims.

What is claimed is:

1. A tetracycline regulated retroviral vector for expressing a coding sequence, the vector comprising the following DNA sequences operatively linked from 5' to 3':
   (a) DNA comprising a first promoter;
   (b) DNA comprising a second promoter different from the first promoter in (a) and different from the third promoter in (e);
   (c) DNA encoding a tetracycline regulator unit (tTA) under the transcriptional control of said second promoter;
   (d) DNA comprising a tetracycline response unit (tetO) in an antisense orientation relative to said DNA encoding said regulator unit of (c); and
   (e) DNA comprising a third promoter different from the first promoter in (a) and different from the second promoter in (b) wherein said DNA comprising said response unit of (d) is comprised within said third promoter,
   wherein a coding sequence can be incorporated into the vector and operably linked to the third promoter of (e).

2. The vector of claim 1 wherein the first promoter of (a) is specific for a cell type that said vector infects.

3. The vector of claim 1 wherein the first promoter of (a) is specific for a tissue type that said vector infects.

4. The vector of claim 1 wherein said first promoter of (a) is selected from the group consisting of a 5' retroviral long terminal repeat promoter, a Rous Sarcoma Virus (RSV) promoter, a Human Immunodeficiency Virus (HIV) promoter, and a phosphoglycerate kinase promoter.

5. The vector of claim 1 further comprising DNA encoding a mammalian protein selected from the group consisting of ICE, GDNF, and TH, and wherein said DNA encoding the mammalian protein is under the transcriptional control of said third promoter of (e).

6. The vector of claim 5 wherein the addition of tetracycline to a growth medium comprising a cell comprising said vector increases or enhances the expression of said DNA encoding said mammalian protein, as compared with the level of expression in the absence of tetracycline.

7. The vector of claim 5 wherein the addition of tetracycline to a growth medium comprising a cell comprising said vector inhibits or suppresses the expression of said DNA encoding said mammalian protein, as compared with the level of expression in the absence of tetracycline.

8. The vector of claim 1 wherein said second promoter of (b) is selected from the group consisting of a SV40 promoter, a JC virus promoter, a glial fibrillary promomter, a nestin promoter, a P0 promoter, an estrogen receptor promoter, and a phosphoglycerate kinase promoter.

9. The vector of claim 1 wherein said third promoter of (e) is selected from the group consisting of a CMV promoter and a thymidine kinase promoter.

10. The vector of claim 1, further comprising an endonuclease site.

11. The vector of claim 10 wherein said endonuclease site is selected from the group consisting of XhoI, SpeI, SfiI, and BstxI endonuclease sites.

12. The vector of claim 1 further comprising a DNA encoding a selectable marker, under the transcriptional control of said first promoter in (a).

13. The vector of claim 12 wherein said selectable marker is selected from the group consisting of puromycin, neomycin, hygromycin and thymidine kinase.

14. A tetracycline regulated retroviral vector for expressing a coding sequence, the vector comprising the following DNA sequences operatively linked from 5' to 3':
   (a) DNA comprising a first promoter;
   (b) DNA encoding a selectable marker under the transcriptional control of said first promoter in (a);
   (c) DNA comprising a second promoter different from the first promoter in (a) and different from the third promoter in (g);
   (d) DNA encoding a tetracycline regulator unit (tTA) under the transcriptional control of said second promoter;
   (e) an endonuclease site;
   (f) DNA comprising a tetracycline response unit (tetO) in an antisense orientation relative to said DNA encoding said regulator unit of (d); and
   (g) DNA comprising a third promoter different from the first promoter in (a) and different from the second promoter in (c) wherein said DNA comprising said response unit of (f) is comprised within said third promoter,
   wherein a coding sequence can be incorporated into the vector and operably linked to the third promoter of (g).

15. The vector of claim 14 wherein the first promoter of (a) is specific for a cell type that said vector infects.

16. The vector of claim 14 wherein the first promoter of (a) is specific for a tissue type that said vector infects.

17. The vector of claim 14 wherein said first promoter of (a) is selected from the group consisting of a 5' retroviral long terminal repeat promoter, a Rous Sarcoma Virus promoter, a phosphoglycerate kinase promoter, and a Human Immunodeficiency Virus promoter.

18. The vector of claim 14 further comprising DNA encoding a mammalian protein selected from the group consisting of ICE, GDNF, and TH, wherein said DNA encoding the mammalian protein is under the transcriptional control of said third promoter of (e).

19. The vector of claim 18 wherein the addition of tetracycline to a growth medium comprising a cell comprising said vector increases or enhances the expression of said DNA encoding said mammalian protein, as compared with the level of expression in the absence of tetracycline.

20. The vector of claim 18 wherein the addition of tetracycline to a growth medium comprising a cell comprising said vector inhibits or suppresses the expression of said DNA encoding said mammalian protein, as compared with the level of expression in the absence of tetracycline.

21. The vector of claim 14, wherein said second promoter of (c) is selected from the group consisting of an SV40 promoter, a JC virus promoter, a glial fibrillary acidic protein promoter, a nestin promoter, a P0 promoter, an estrogen receptor promoter, and a phosphoglycerate kinase promoter.

22. The vector of claim 14 wherein said third promoter of (g) is selected from the group consisting of a CMV promoter and a thymidine kinase promoter.

23. The vector of claim 14 wherein said endonuclease site of (e) is selected from the group consisting of XhoI, SpeI, SfiI, and BstxI endonuclease sites.

24. The vector of claim 14, wherein said selectable marker of (b) is selected from the group consisting of puromycin resistance, hygromycin resistance, neomycin resistance and thymidine kinase.

25. The vector of claim 14 wherein said first promoter is the 5' retroviral long terminal repeat promoter, said selectable marker is puromycin resistance, said second promoter of (c) is selected from the group consisting of SV40 promoter and JC virus promoter, and wherein said third promoter of (g) is CMV promoter.

26. An in vitro method of making a cell susceptible to apoptosis in vitro, comprising the steps of:
   (a) providing a tetracycline regulated retroviral vector of claim 1, wherein the vector comprises DNA encoding the IL-1 Beta-converting enzyme (ICE), or a functional homologue of ICE, under the transcriptional control of tetracycline;
   (b) introducing said vector into said cell in vitro; and
   (c) maintaining said cell in vitro under conditions such that the DNA encoding ICE or a functional homologue of ICE is expressed at a level sufficient to induce apoptosis of said cell.

27. The method of claim 26 wherein the presence of tetracycline in a growth medium comprising said cell inhibits or suppresses expression of said ICE encoding DNA, as compared with the level of expression in the absence of tetracycline.

28. The method of claim 26 wherein the presence of tetracycline in a growth medium comprising said cell enhances or increases expression of said ICE encoding DNA, as compared with the level of expression in the absence of tetracycline.

29. A method of expressing a regulatable or inducible gene in a cell in vitro, comprising the steps of:
   (a) providing a viral particle comprising a tetracycline regulated retroviral vector of claim 1, wherein the vector comprises said gene;
   (b) administering said viral particle to said cell in vitro; and
   (c) allowing expression of the gene in vitro.

30. The method of claim 29 wherein said gene encodes a protein selected from the group consisting of ICE, tyrosine hydroxylase, and glial-derived neurotropic factor.

31. A method of making a cell in vitro susceptible to apoptosis, comprising the steps of:
   (a) providing a tetracycline regulated retroviral vector of claim 14, wherein the vector comprises DNA encoding the IL-1 Beta-converting enzyme (ICE), or a functional homologue of ICE, under the transcriptional control of tetracycline;
   (b) introducing said vector into said cell in vitro; and
   (c) maintaining said cell in vitro under conditions such that the DNA encoding ICE or a functional homologue of ICE is expressed at a level sufficient to induce apoptosis of the cell.

32. A method of expressing a regulatable or inducible gene in a cell in Vitro, comprising the steps of:
   (a) providing a cell in vitro;
   (b) introducing into said cell of (a) a tetracycline regulated retroviral vector of claim 14, wherein the vector comprises said gene, and wherein said gene is under the transcriptional control of tetracycline; and
   (c) allowing expression of the gene in vitro.

33. A method of expressing a regulatable or inducible gene in a cell in vitro, comprising the steps of:
   (a) providing a viral particle comprising a tetracycline regulated retroviral vector of claim 14, wherein the vector comprises said gene;
   (b) administering said viral particle to said cell in vitro; and
   (c) allowing expression of the gene in vitro.

34. The vector of claim 1, further comprising a coding sequence operatively linked to the third promoter of (e).

35. The vector of claim 14, further comprising a coding sequence operatively linked to the third promoter of (g).

* * * * *

```
                              SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:1:

GGCCGCTTAA TTAAGTTTAA ACG                                           23

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:2:

GATCCGTTTA AACTTAATTA AGCGGCCG                                      28

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

GATCCCCCGG G                                                        11

(2) INFORMATION FOR SEQ ID NO:4:

(i) SEQUENCE CHARACTERISTICS:
        (A) LENGTH: 7 base pairs
        (B) TYPE: nucleic acid
        (C) STRANDEDNESS: single
        (D) TOPOLOGY: linear
```

```
(ii) MOLECULE TYPE: Genomic DNA (xi) SEQUENCE DESCRIPTION: SEQ ID NO:4:

CCCGGGG                                                                                        7
```